(12) United States Patent
Ahn et al.

(10) Patent No.: US 8,992,886 B2
(45) Date of Patent: Mar. 31, 2015

(54) CYCLIC PEPTIDE ANALOGUES FOR NON-INVASIVE IMAGING OF PANCREATIC BETA-CELLS

(75) Inventors: Jung-Mo Ahn, Plano, TX (US); Xiankai Sun, Coppell, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 1 day.

(21) Appl. No.: 13/263,320

(22) PCT Filed: Apr. 6, 2010

(86) PCT No.: PCT/US2010/030103
§ 371 (c)(1),
(2), (4) Date: Nov. 22, 2011

(87) PCT Pub. No.: WO2010/118034
PCT Pub. Date: Oct. 14, 2010

(65) Prior Publication Data
US 2012/0100070 A1    Apr. 26, 2012

Related U.S. Application Data

(60) Provisional application No. 61/166,942, filed on Apr. 6, 2009.

(51) Int. Cl.
| C07K 14/06 | (2006.01) |
| A61K 51/08 | (2006.01) |
| A61K 49/14 | (2006.01) |
| A61B 5/055 | (2006.01) |

(52) U.S. Cl.
CPC .................................. *A61K 51/088* (2013.01)
USPC ......... 424/1.69; 424/9.6; 424/9.341; 424/9.1; 530/308

(58) Field of Classification Search
None
See application file for complete search history.

(56) References Cited

U.S. PATENT DOCUMENTS

2008/0300193 A1   12/2008   Ahn et al.
2011/0166062 A1*  7/2011    Dimarchi et al. .............. 514/5.3

FOREIGN PATENT DOCUMENTS

| WO | WO2003/011892 A1 * | 2/2003 | .......... C07K 14/575 |
| WO | 2006024275 A2 | 3/2006 | |
| WO | 2007124461 A1 | 11/2007 | |

OTHER PUBLICATIONS

Wild et al., "[Lys40(Ahx-DTPA-111In)NH2]Exendin-4, a Very Promising Ligand for Glucagon-like Peptide-1 (GLP-1) Receptor Targeting," The Journal of Nuclear Medicine, (2006) 47(12):2025-2033.*
Deacon et al., "Dipeptidyl peptidase IV resistant analogues of glucagon-like peptide-1 which have extended metabolic stability and improved biological activity," Diabetologia (1998) 41:271-278.*
Pakkala et al, "Activity and stability of human kallikrein-2-specific linear and cyclic peptide inhibitors," J. Pept. Sci. 2007: 13:348-353.*
Murage, "Solid-Phase Synthesis of Alpha Helix-Stabilized Glucagon-Like Peptide-1 Analogues via Lactam Bridge Formation," University of Texas at Dallas, May, 2008.*
Bracken et al., Synthesis and Nuclear Magnetic Resonance Structure Determination of an α-Helical, Bicyclic, Lactam-Bridged Hexapeptide, J. Am. Chem. Soc. 1994, 116, 6431-6432.*
Miao et al., 111In-Labeled Lactam Bridge-Cyclized α-Melanocyte Stimulating Hormone Peptide Analogues for Melanoma Imaging, Bioconjugate Chem., 2008, 19, 539-547.*
Wicki, Andreas, et al., "[Lys40(Ahx-DTPA-111In)NH2]-Exendin-4 is a Highly Efficient Radiotherapeutic for GlucagonLike Peptide-1 Receptor-Targeted Therapy for Insulinoma," Clinical Cancer Research, (2007), 13:3696-3705.
Wild, Damian, et al., "[Lys40(Ahx-DTPA-111In)NH2]Exendin-4, a Very Promising Ligand for Glucagon-like Peptide-1 (GLP-1) Receptor Targeting," J Nucl Med, (2006), 47:2025-2033.
International Search Report and Written Opinion for PCT/US2010/030103, dated Jan. 21, 2011.

* cited by examiner

*Primary Examiner* — Karlheinz R Skowronek
*Assistant Examiner* — Joseph Fischer
(74) *Attorney, Agent, or Firm* — Parker Highlander PLLC

(57) ABSTRACT

Compositions, methods of using and methods of making a cyclic peptide analog imaging agent that includes at least portions of a peptide or protein that binds specifically to the GLP-1 receptor (GLP-1R) and the cyclic analog has one or more conformational restrictions including, but not limited to, lactam bridges, disulfide bridges, hydrocarbon bridges, and their combinations, salts and derivatives thereof wherein the cyclic analog is more stable than a non-cyclic analog when incubated in the presence of enzymes that degrade GLP-1 and have an increased serum half-live, wherein the cyclic analog comprises at least a portion of a GLP-1 peptide or at least a portion of an Exendin peptide salts, derivatives or combinations thereof.

25 Claims, 10 Drawing Sheets
(2 of 10 Drawing Sheet(s) Filed in Color)

| PEPTIDE | SEQUENCE | SEQUENCE IDENTIFICATION NUMBER | EC$_{50}$ (nM) |
|---|---|---|---|
| [D-Ala8]GLP-1 | HaEGTFTSDVSSYLEGQAAKEFIAWLVKGR* | 4   30 | 4.7 |
| c[Glu$^{16}$, Lys$^{20}$]GLP-1 (7-36) NH$_2$ | - - - - - - - - - E - - - K - - - - - - - - - - - - - - | 4   5 | 4.0 |
| c[Glu$^{30}$, Lys$^{34}$]GLP-1 (7-36)- NH$_2$ | - - - - - - - - - - - - - - - - - - - - - - - E - - - K - - | 4   6 | 5.8 |
| c[Glu$^{16}$, Lys$^{20}$]-c[Glu$^{30}$, Lys$^{34}$]GLP-1 (7-36)- NH$_2$ | - - - - - - - - - E - - - K - - - - - - - - - E - - - K - - | 4   7 | 3.3 |
| c[Glu$^{18}$, Lys$^{22}$]-c[Glu$^{30}$, Lys$^{34}$]GLP-1 (7-36)- NH$_2$ (EM2198) | - - - - - - - - - - - E - - - K - - - - - - - E - - - K - - | 4   8 | 1.2 |

* THIS PEPTIDES MAY ALSO INCLUDE A C-TERMINUS AMINOHEXANOIC ACID GROUP

CYCLIC PEPTIDE ANALOGUES FOR NON-INVASIVE IMAGING OF PANCREATIC BETA-CELLS

CROSS-REFERENCE TO RELATED APPLICATIONS

This application is a U.S. National Phase Application of International Application No. PCT/US2010/030103, filed Apr. 6, 2010, which claims the benefit of U.S. Provisional Application No. 61/166,942, filed Apr. 6, 2009.

STATEMENT OF FEDERALLY FUNDED RESEARCH

This invention was made with U.S. Government support under Contract No. P01 DK058398-06 awarded by the NIH. The government has certain rights in this invention.

TECHNICAL FIELD OF THE INVENTION

The present invention relates in general to the field of imaging, and more particularly, to novel cyclic glucagon-like peptide and Exendin analogues for non-invasive imaging of pancreatic beta-cells to diagnose, e.g., diabetes mellitus.

BACKGROUND OF THE INVENTION

Without limiting the scope of the invention, its background is described in connection with Diabetes. Diabetes mellitus is a chronic disease characterized by multiple metabolic abnormalities resulting in impaired management of glucose. According to the recent statistics, diabetes is the fifth leading cause of death in the United States. Diabetic patients are also at significantly higher risk to develop complications which severely influence life quality of the patients.

A hallmark of Diabetes is high level of blood glucose caused by the lack of insulin production, insulin resistance in peripheral tissues, or both, and generally classified into two types, insulin-dependent (type 1) and non-insulin-dependent (type 2). Type 1 diabetes is found to be connected with the loss of pancreatic beta-cells which secretes insulin upon feeding. Despite tremendous progress in understanding the basis of diabetes, it still remains unclear which factors are involved in the development of the disease and govern the response to therapeutic intervention. This highlights the need of monitoring the pancreatic beta-cells in body since it will help us to comprehend the development of the disease and the effectiveness of therapeutic treatments.

With recent rapid innovations, molecular imaging is gaining significant attention in the basic biomedical sciences and in clinical research and practice. Indeed, non-invasive imaging techniques are revolutionizing the understanding of diseases at the cellular and molecular levels. However, the conventional magnetic resonance imaging (MRI) and computed tomography (CT) have difficulties to visualize small and soft organs like pancreas, especially the beta-cells.

SUMMARY OF THE INVENTION

The present invention includes novel cyclic glucagon-like peptide (GLP-1) or Exendin analogues used to assess pancreatic beta-cells using non-invasive imaging techniques. GLP-1 sequence includes H$^7$AEGTFTSDVSSYLEGQAAKEFIAWLVKGQR$^{36}$ (SEQ ID No: 1), which is a 30 amino acid-containing peptide that is produced by intestinal L-cells. The Exendin-4 sequence includes H$^1$GEGTFTSDLSKQMEEEAVRLFIEWLKNGGPSSGAPPPS$^{39}$ (SEQ ID No: 2). The cyclic analog comprises a portion of a peptide or protein that binds specifically to the GLP-1 receptor (GLP-1R) and the cyclic analog has one or more conformational restrictions including, but not limited to, lactam bridges, disulfide bridges, hydrocarbon bridges, and their combinations, salts and derivatives thereof wherein the cyclic analog is more stable than a non-cyclic analog when incubated in the presence of enzymes that degrade GLP-1 and have an increased serum half-live.

The present invention includes novel cyclic GLP-1 analogues used to assess pancreatic beta-cells using non-invasive imaging techniques. GLP-1 is an endogenous hormone that is known to interact with a receptor on the pancreatic beta-cells. However, rapid enzymatic degradation of this peptide in vivo prevents its effective use. The novel cyclic GLP-1 analogues are extremely stable against enzymes that are known to participate in the GLP-1 degradation. In addition, these cyclic GLP-1 analogues were found to have higher potency when compared to the native GLP-1. Using these enzymatically stable GLP-1 analogues, PET (positron emission tomography) imaging agents were produced and detected pancreatic beta-cells in vivo. These molecular imaging probes are of great value in diagnosing diabetes, monitoring the progress of the disease, and evaluating effectiveness of therapeutic treatment of the disease.

In one embodiment, the present invention includes composition, methods and agents comprising at least portions of GLP-1 with one or more conformational restrictions, including, but not limited to, lactam bridges, disulfide bridges, hydrocarbon bridges, and their combinations, between the positions 7 and 36 of GLP-1, salts and derivatives thereof wherein the agent is more stable than a non-cyclic analog when incubated in the presence of enzymes that degrade GLP-1 and have an increased serum half-live. In one aspect, the agent is selected from at least one of:

HAEGTFTSDESSYKEGQAAKEFIAWLVKG R (SEQ ID No: 5)
HAEGTFTSDVSSYLEGQAAKEFIEWLVKG R (SEQ ID No: 6)
HAEGTFTSDESSYKEGQAAKEFIEWLVKG R (SEQ ID No: 7)
HAEGTFTSDVSEYLEKQQAAKEFIEWLVKG R (SEQ ID No: 8)
HXEGTFTSDESSYKEGQAAKEFIAWLVKG R, wherein X is D-Ala (SEQ ID No: 9)
HXEGTFTSDVSSYLEGQAAKEFIEWLVKG R, wherein X is D-Ala, (SEQ ID No: 10)
HXEGTFTSDESSYKEGQAAKEFIEWLVKG R, wherein X is D-Ala (SEQ ID No: 11)
HXEGTFTSDVSEYLEKQAAKEFIEWLVK R, wherein X is D-Ala (SEQ ID No: 12)
HAEQTFTSDVSEYLEKQAAKEFIAWLVK GR (SEQ ID No: 13)
HXEGTFTSDVSEYLEKQAAKEFIAWLVK GR, wherein X is D-Ala (SEQ ID No: 14)
HXEGTFTSDESSYKEGQAAKEFIAWLVKG R, wherein X is AiB (2-Aminoisobutyric acid) (SEQ ID No: 15)
HXEGTFTSDVSEYLEKQAAKEFIAWLVK G, wherein X is AiB, (SEQ ID No: 16)
HXEGTFTSDVSSYLEGQAAKEFIEWLVKG R, wherein X is AiB (2-Aminoisobutyric acid) (SEQ ID No: 17)
HXEGTFTSDESSYKEGQAAKEFIEWLVKG R, wherein X is AiB (2-Aminoisobutyric acid, (SEQ ID No: 18) and
HXEGTFTSDVSEYLEKQAAKEFIEWLVKG R, wherein X is AiB (2-Aminoisobutyric acid) (SEQ ID No: 19), and salts or derivatives thereof. In one aspect, the agent binds specifically to the GLP-1 receptor. In one aspect, the agent is multivalent. In one aspect, the agent further comprises at least one of a radiolabel, an enzyme, a fluorescent label, a luminescent label, a bioluminescent label, a magnetic label, and biotin. In one aspect, the agent further comprises at least one of $^{18}$F, $^{68}$Ga, $^{60/61/62/64}$Cu, $^{89}$Zr, $^{86}$Y, $^{124}$I, $^{99m}$Tc, $^{94m}$Tc, $^{111}$In, $^{67}$Ga, $^{125}$I, $^{123}$I, $^{177}$Lu, $^{75/76/77}$Br, $^{166}$Ho, and $^{153}$Sm. In one aspect, the agent further comprises at least one of a therapeutic or cytotoxic agent.

In one aspect, the agent further comprises at least one of an anti-metabolite, an alkylating agent, an antibiotic, a growth factor, a cytokine, an anti-angiogenic agent, an anti-mitotic agent, an anthracycline, toxin, and an apoptotic agent. In one aspect, the imaging agent binds specifically to pancreatic tissue. In one aspect, the imaging agent further comprises a pharmaceutically acceptable excipient. In one aspect, the imaging agent is formulated for use in a diagnostic method practiced on the human or animal body. In one aspect, the imaging agent has an increased resistance to proteolytic cleavage by dipeptidyl peptidase-IV (DPP-IV), neutral endopeptidase (NEP), or both. In one aspect, the imaging agent is an organ specific imaging agent comprises one or more labels that made the agent detectable by positron emission tomography (PET), single photon emission computed tomography (SPECT), radioscintigraphy, or magnetic resonance imaging (MRI). In one aspect, the imaging agent is adapted for imaging pancreatic beta cells.

In another embodiment, the present invention includes composition, methods and agents for imaging a pancreas comprising: injecting into a patient in need of pancreatic imaging an effective amount of a contract agent comprising at least a portion of GLP-1 with one or more conformational restrictions, including but not limited to, lactam bridges, disulfide bridges, hydrocarbon bridges, and their combinations, between the positions 7 and 36 of GLP-1, salts and derivatives thereof. wherein the agent is more stable than a non-cyclic analog when incubated in the presence of enzymes that degrade GLP-1 and have an increased serum half-live. In one aspect, the agent is selected from at least one of:

HAEGTFTSDESSYKEGQAAKEFIAWLVKG R (SEQ ID No: 5)
HAEGTFTSDVSSYLEGQAAKEFIEWLVKG R (SEQ ID No: 6)
HAEGTFTSDESSYKEGQAAKEFIEWLVKG R (SEQ ID No: 7)
HAEGTFTSDVSEYLEKGQAAKEFIEWLVKG R (SEQ ID No: 8)
HXEGTFTSDESSYKEGQAAKEFIAWLVKG R, wherein X is D-Ala (SEQ ID No: 9)
HXEGTFTSDVSSYLEGQAAKEFIEWLVKG R, wherein X is D-Ala, (SEQ ID No: 10)
HXEGTFTSDESSYKEGQAAKEFIEWLVKG R, wherein X is D-Ala (SEQ ID No: 11)
HXEGTFTSDVSEYLEKQAAKEFIEWLVKG R, wherein X is D-Ala (SEQ ID No: 12)
HAEGTFTSDVSEYLEKQAAKEFIAWLVK GR (SEQ ID No: 13)
HXEQTFTSDVSEYLEKAAKEFIAWLVK GR, wherein X is D-Ala (SEQ ID No: 14).
HXEGTFTSDESSYKEGQAAKEFIAWLVKQ R, wherein X is AiB (2-Aminoisobutyric acid) (SEQ ID No: 15)
HXETFTSDVSEYLEKAAKEFIAWLVK GR, wherein X is AiB, (SEQ ID No: 16)
HXEGTFTSDVSSYLEGQAAKEFIEWLVKQ R, wherein X is AiB (2-Aminoisobutyric acid) (SEQ ID No: 17)
HXEGTFTSDESSYKEQQAAKEFIEWLVKQ R, wherein X is AiB (2-Aminoisobutyric acid, (SEQ ID No: 18) and HXEGTFTSDVSEYLEKQAAKEFIEWLVKQ R, wherein X is AiB (2-Aminoisobutyric acid) (SEQ ID No: 19), and salts or derivatives thereof. In one aspect, the agent binds specifically to the GLP-1 receptor. In one aspect, the agent is multivalent. In one aspect, the agent further comprises at least one of a radiolabel, an enzyme, a fluorescent label, a luminescent label, a bioluminescent label, a magnetic label, and biotin. In one aspect, the agent further comprises at least one of $^{18}$F, $^{68}$Ga, $^{60/61/62/64}$Cu, $^{89}$Zr, $^{86}$Y, $^{124}$I, $^{99m}$Tc, $^{94m}$Tc, $^{111}$In, $^{67}$Ga, $^{125}$I, $^{123}$I, $^{177}$Lu, $^{75/76/77}$Br, $^{166}$Ho, and $^{153}$Sm. In one aspect, the agent further comprises at least one of a therapeutic or cytotoxic agent. In one aspect, the agent further comprises at least one of an anti-metabolite, an alkylating agent, an antibiotic, a growth factor, a cytokine, an anti-angiogenic agent, an anti-mitotic agent, an anthracycline, toxin, and an apoptotic agent.

In one aspect, the imaging agent binds specifically to pancreatic tissue. In one aspect, the imaging agent further comprises a pharmaceutically acceptable excipient. In one aspect, the imaging agent is formulated for use in a diagnostic method practiced on the human or animal body. In one aspect, the imaging agent has an increased resistance to proteolytic cleavage by dipeptidyl peptidase-IV (DPP-IV), neutral endopeptidase (NEP), or both. In one aspect, the imaging agent is an organ specific imaging agent comprises one or more labels that made the agent detectable by positron emission tomography (PET), single photon emission computed tomography (SPECT), radioscintigraphy, or magnetic resonance imaging (MRI).

In another embodiment, the present invention includes an imaging agent comprising at least one of:

HAEGTFTSDESSYKEGQAAKEFIAWLVKG R (SEQ ID No: 5)
HAEGTFTSDVSSYLEGQAAKEFIEWLVKG R (SEQ ID No: 6)
HAEGTFTSDESSYKEGQAAKEFIEWLVKG R (SEQ ID No: 7)
HAEQTFTSDVSEYLEKQAAKEFIEWLVKG R (SEQ ID No: 8)
HXEGTFTSDESSYKEGQAAKEFIAWLVKG R, wherein X is D-Ala (SEQ ID No: 9)
HXEGTFTSDVSSYLEGQAAKEFIEWLVKQ R, wherein X is D-Ala, (SEQ ID No: 10)
HXEGTFTSDESSYKEGQAAKEFIEWLVKQ R, wherein X is D-Ala (SEQ ID No: 11)
HXEGTFTSDVSEYLEKQAAKEFIEWLVKQ R, wherein X is D-Ala (SEQ ID No: 12)
HAEQTFTSDVSEYLEKQAAKEFIAWLVK GR (SEQ ID No: 13)
HXEGTFTSDVSEYLEKQAAKEFIAWLVK GR, wherein X is D-Ala (SEQ ID No: 14)
HXEGTFTSDESSYKEGQAAKEFIAWLVKQ R, wherein X is AiB (2-Aminoisobutyric acid) (SEQ ID No: 15)
HXEGTFTSDVSEYLEKQAAKEFIAWLVK GR, wherein X is AiB, (SEQ ID No: 16)
HXEGTFTSDVSSYLEGQAAKEFIEWLVKG R, wherein X is AiB (2-Aminoisobutyric acid) (SEQ ID No: 17)
HXEGTFTSDESSYKEGQAAKEFIEWLVKG R, wherein X is AiB (2-Aminoisobutyric acid, (SEQ ID No: 18) and
HXEGTFTSDVSEYLEKAAKEFIEWLVKG R, wherein X is AiB (2-Aminoisobutyric acid) (SEQ ID No: 19) and salts or derivatives thereof, wherein the agent is more stable than a non-cyclic analog when incubated in the presence of enzymes that degrade GLP-1 and have an increased serum half-live. In one aspect, the agent binds specifically to the GLP-1 receptor. In one aspect, the agent is multivalent. In one aspect, the agent further comprises at least one of a radiolabel, an enzyme, a fluorescent label, a luminescent label, a bioluminescent label, a magnetic label, and biotin. In one aspect, the agent further comprises at least one of $^{18}$F, $^{68}$Ga, $^{60/61/62/64}$Cu, $^{89}$Zr, $^{86}$Y, $^{124}$I, $^{99m}$Tc, $^{94m}$Tc, $^{111}$In, $^{67}$Ga, $^{125}$I, $^{123}$I, $^{177}$Lu, $^{75/76/77}$Br, $^{166}$Ho, and $^{153}$Sm. In one aspect, the agent further comprises at least one of a therapeutic or cytotoxic agent, e.g., an anti-metabolite, an alkylating agent, an antibiotic, a growth factor, a cytokine, an anti-angiogenic agent, an anti-mitotic agent, an anthracycline, toxin, and an apoptotic agent. In one aspect, the imaging agent binds specifically to pancreatic tissue. In one aspect, the imaging agent further comprises a pharmaceutically acceptable excipient. In one aspect, the imaging agent is formulated for use in a diagnostic method practiced on the human or animal body. In one aspect, the imaging agent has an increased resistance to proteolytic cleavage by dipeptidyl peptidase-IV (DPP-IV), neutral endopeptidase (NEP), or both. In one aspect, the imaging agent is an organ specific imaging agent comprises one or more labels that made the agent detectable by positron emission tomography (PET), single photon emission computed tomography (SPECT), radioscintigraphy, or magnetic resonance imaging (MRI).

One embodiment of the present invention includes a multivalent GLP-1 having an optionally substituted multivalent composition conjugated to two or more GLP-1 molecules to form the multivalent GLP-1, wherein the multivalent GLP-1 is more stable than a non-cyclic analog when incubated in the presence of enzymes that degrade GLP-1 and have an increased serum half-live.

In another embodiment, the present invention includes a diagnostic or imaging agent comprising HXETFTSDVSEYLEKQAAKEFIEWLVKG R, wherein X is D-Ala (SEQ ID No: 12), salts or derivatives thereof. In one aspect, the agent is multivalent.

The present invention includes a composition having an agent comprising at least portions of an Exendin-4 protein having one or more conformational restrictions including, but not limited to, lactam bridges, disulfide bridges, hydrocarbon bridges, and their combinations, salts and derivatives thereof wherein the agent is more stable than a non-cyclic analog when incubated in the presence of enzymes that degrade GLP-1 and have an increased serum half-live.

The present invention includes a diagnostic or imaging agent having at least one of: a cyclic analog imaging agent comprising a portion of a peptide or protein that binds specifically to the GLP-1 receptor (GLP-1R) and the cyclic analog has one or more conformational restrictions including, but not limited to, lactam bridges, disulfide bridges, hydrocarbon bridges, and their combinations, salts and derivatives thereof wherein the cyclic analog is more stable than a non-cyclic analog when incubated in the presence of enzymes that degrade GLP-1 and have an increased serum half-live, wherein the cyclic analog comprises at least a portion of a GLP-1 peptide or at least a portion of an Exendin-4 peptide salts, derivatives or combinations thereof In one aspect, the agent is selected from at least one of:
HGEGTFTSDESKQKEEEAVRL FIEWLKNGGPSSGAPPPS (SEQ ID No: 20); HGEGTFTSDLSKQMEEEAVR LFIEWLKKGGPSSGAPPPS (SEQ ID No: 21); HGEGTFTSDLSEQMEKEAVR LFIEWLKNGGPSSGAPPPS (SEQ ID No: 22); HGEGTFTSDESKQKEEEAVRL FIEWLKKGGPSSGAPPPS (SEQ ID No: 23); HGEGTFTSDLSEQMEKEAVR LFIEWLKKGGPSSGAPPPS (SEQ ID No: 24);
HGEGTFTXDESKQKEEEAVR LFIEWLKNGGPSSGAPPPS, wherein X is AiB, 2-Aminoisobutyric acid, (SEQ ID No: 25);
HGEGTFTXDLSEQMEKEAVR LFIEWLKNGGPSSGAPPPS, wherein X is AiB (2-Aminoisobutyric acid) (SEQ ID No: 26);
HGEGTFTXDLSKQMEEEAVR LFIEWLKKGGPSSGAPPPS, wherein X is AiB (2-Aminoisobutyric acid) (SEQ ID No: 27);
HGEGTFTXDESKQKEEEAVR LFIEWLKKGGPSSGAPPPS, wherein X is AiB (2-Aminoisobutyric acid) (SEQ ID No: 28); and
HGEGTFTXDLSEQKEEEAVRL FIEWLKKGGPSSGAPPPS, wherein X is AiB (2-Aminoisobutyric acid) (SEQ ID No: 29) and salts or derivatives thereof. In one aspect, the agent binds specifically to the GLP-1 receptor. In one aspect, the agent is multivalent. In one aspect, the agent further comprises at least one of a radiolabel, an enzyme, a fluorescent label, a luminescent label, a bioluminescent label, a magnetic label, and biotin. In one aspect, the agent further comprises at least one of $^{18}$F, $^{68}$Ga, $^{60/61/62/64}$Cu, $^{89}$Zr, $^{86}$Y, $^{124}$I, $^{99m}$Tc, $^{111}$In, $^{67}$Ga, $^{125}$I, $^{123}$I, $^{177}$Lu, $^{166}$Ho, and $^{153}$Sm. In one aspect, the agent further comprises at least one of a therapeutic or cytotoxic agent.

BRIEF DESCRIPTION OF THE DRAWINGS

For a more complete understanding of the features of advantages of the present invention, reference is now made to the detailed description of the invention along with the accompanying figures. The patent or application file contains at least one drawing executed in color. Copies of this patent or patent application publication with color drawing(s) will be provided by the Office upon request and payment of the necessary fee. In which:

FIG. 3 is a chart that shows receptor activation by cyclic GLP-1 analogues

DETAILED DESCRIPTION OF THE INVENTION

Figure 1:
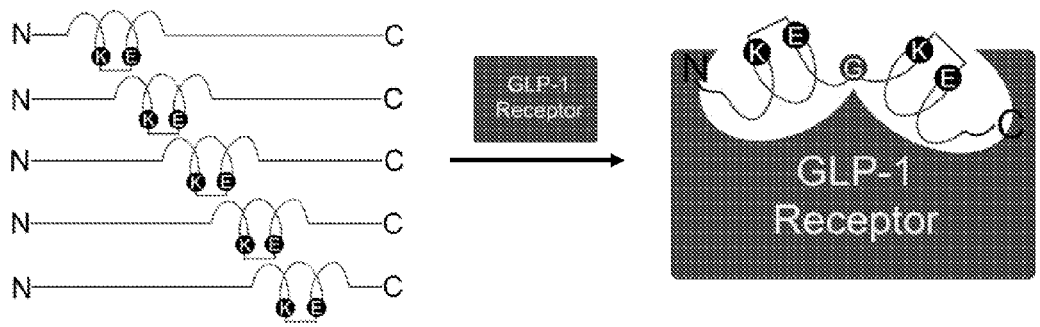
FIG. 1 is a diagram that shows the introduction of a lactam bridge to GLP-1, and the enhanced binding obtained with the bicyclic GLP-1 analogues of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention finds particular uses in the assessment of functional pancreatic beta-cells is essential for diagnosis and prognosis of, e.g., diabetes, as well as prevention of the disease and evaluation of effectiveness of therapeutic treatment. However, no reliable methods have been developed yet to measure human pancreatic beta-cell mass in vivo. As a biomarker, GLP-1 appears to be a good candidate, but rapid enzymatic degradation is significant obstacle for developing effective molecular imaging probes using it. To solve this problem, novel cyclic GLP-1 analogues were designed and synthesized that were found to show significantly improved stability against enzymatic degradation. In addition, the cyclic structure enhanced the potency of the cyclic GLP-1 analogues that allowed clear detection of pancreatic beta-cells.

The developed of these novel cyclic GLP-1 analogues as molecular imaging agents allows early detection of, e.g., diabetes; easy monitoring of the progress of the disease; and facile evaluation of therapeutic treatment of the disease. Thus, this is of great value to pre-diabetic patients who show high potential to become diabetic for early detection and early treatment; and diabetic patients who are already diagnosed and taking medications to determine the effectiveness of drugs.

The novel cyclic GLP-1 analogues can be labeled with proteins, radionuclides, fluorescent labels, metals, chromogenic agents, enzymes and other agents that enhace its use as an imaging agents. Examples of radionuclides include, e.g., $^{18}F$, $^{68}Ga$, $^{60/61/62/64}Cu$, $^{89}Zr$, $^{86}Y$, $^{124}I$, $^{99m}Tc$, $^{94m}Tc$, $^{111}In$, $^{67}Ga$, $^{125}I$, $^{123}I$, $^{177}Lu$, $^{75/76/77}Br$, $^{166}Ho$, and $^{153}Sm$. the imaging agent further comprises at least one of a radiolabel, an enzyme, a fluorescent label, a luminescent label, a bioluminescent label, a magnetic label, and biotin. The agent further comprises at least one of an anti-metabolite, an alkylating agent, an antibiotic, a growth factor, a cytokine, an anti-angiogenic agent, an anti-mitotic agent, an anthracycline, toxin, and an apoptotic agent. The imaging agent may include or more labels that make the agent detectable by positron emission tomography (PET), single photon emission computed tomography (SPECT), radioscintigraphy, magnetic resonance imaging (MRI) and computed tomography (CT scan). The agents disclosed herein have been found to have increased resistance to proteolytic cleavage by dipeptidyl peptidase-IV (DPP-IV), neutral endopeptidase (NEP), or both.

Among many molecules that interact with pancreatic beta-cells, glucagon-like peptide-1 (GLP-1) is found to be highly relevant to the functions of the beta-cells since it stimulates insulin secretion and proliferation of the beta-cells. Thus, it may be an ideal candidate to be employed for non-invasive imaging of the beta-cells. However, its rapid metabolism hampers the use of GLP-1 as in vivo imaging agents. In addition, the limited number of GLP-1 receptors on the beta-cells requires high specificity and sensitivity for imaging studies.

With recent technical innovations in various imaging modalities, molecular imaging is gaining significant attention in the basic biomedical sciences and in clinical research and practice. Indeed, non-invasive imaging techniques are revolutionizing the understanding of diseases at the cellular and molecular levels. The ability to non-invasively visualize pancreatic beta-cells would greatly facilitate the development of new methods in the prevention and treatment of diabetes. Conventional magnetic resonance imaging (MRI) and computed tomography (CT) can be used to delineate the location of the pancreas in a subject at a spatial resolution of <100 μm. However, it is extremely difficult if not impossible, for these two modalities to differentiate the islets of Langerhans from other pancreatic tissues because pancreas is a highly vascularized soft organ and the islets only represent 2-3% of the pancreatic tissues. In order to visualize the beta-cells in the islets of Langerhans, imaging or contrast agents that recognize the scarcely dispensed beta-cells within pancreas and are responsive to their biological functions, must be developed.

Among currently available imaging modalities, tomographic nuclear imaging approaches, especially positron emission tomography (PET), have demonstrated their significant importance and promising potential in applications of molecular imaging probes due to the superior sensitivity and specificity in diverse subjects, and the ability to quantitatively analyze the regions of interest (2-5). Represented by successful PET imaging of normal pancreas in three mammalian species with $^{18}F$-labeled FBT (4-$^{18}F$-fluoro-benzyltrozamicol), diabetic pancreas in rats with $^{11}C$-labeled DTBZ (dihydrotetrabenazine), and clinical differentiation of focal and diffuse hyperinsulinism with $^{18}F$-labeled L-DOPA (L-3,4-dihydroxyphenylalanine), PET imaging methods have gained a considerable momentum to move forward to the molecular imaging of the pancreatic beta-cells.

With the superior inherent sensitivity, PET imaging techniques can be mainly defined by the successful development of radiotracers that specifically target the pancreatic beta-cells. Monoclonal antibodies and peptides which are specific to cell membrane receptors have been used as targeting molecules for cancer diagnosis and therapy (6,7). Compared to monoclonal antibodies, peptides have shown more efficient tissue penetration and rapid clearance from non-target organs, and normally are not immunogenic upon repetitive administration.

Among many peptides known to interact with pancreatic beta-cells, glucagon-like peptide-1 (GLP-1) plays a critical role in the function of beta-cells. GLP-1 (sequence: H$^7$AEGTFTSDVSSYLEGQAAKEFIAWLV KGR$^{36}$; SEQ ID No: 1) is a 30 amino acid-containing peptide that is produced by intestinal L-cells. Its predominant bioactive form is GLP-1(7-36) amide, which is considered as the endogenous ligand to the GLP-1 receptor (8). In response to feeding, GLP-1 is secreted from intestinal L-cells into the blood stream (8-10). The circulating hormone acts on pancreatic beta-cell GLP-1 receptors, and enhances glucose-stimulated insulin release In addition to its insulinotropic effects, GLP-1 also limits postprandial glucose elevation through several other mechanisms, including (1) stimulation of beta-cell growth and survival (13,14); (2) inhibition of glucagon release from pancreatic alpha-cells (15); (3) delay of gastric emptying via vagal mechanisms (16,17); and (4) inhibition of short-term food intake by modulation of neuronal activity in the brain (18.19).

GLP-1 receptor (GLP-1R) is a seven transmembrane-spanning G-protein coupled receptor (GPCR), and upon ligand-binding GLP-1R undergo conformational change which leads to the production of secondary messengers including cAMP and $Ca^{2+}$ for its physiological functions. Compared to other members of GPCRs (class A), the size of GLP-1R is large (463 residues) and it employs a long N-terminal chain (120 residues) and large extracellular loops to accommodate its large peptide ligand (20).

Since GLP-1 interacts with its receptor with high binding affinity (Kd<1 nM) and directly involves in the function of the beta-cells, it appears to be a suitable candidate for beta-cell imaging. However, several challenges should be answered in order to develop effective molecular imaging/contrast agents using GLP-1. GLP-1 is highly susceptible to proteases including ubiquitous dipeptidyl-peptidase IV (DPP-IV). This enzyme cleaves two residues (His7-Ala8) from the N-terminus of GLP-1, which are highly important for both of receptor binding and activation. The degradation by DPP-IV results in a fragment, GLP-1(9-36) amide, which lost receptor affinity and biological activity nearly completely. In addition to DPP-IV, neutral endopeptidase (NEP-24.11) is also involved in the metabolism of GLP-1, and these enzymatic degradations result in a half life of <2 min in vivo (8). While several DPP-IV inhibitors have been developed to prevent the metabolism (24), it is still difficult to eliminate this problem.

To suppress or eliminate the enzymatic degradation, we have designed and synthesized a series of cyclic GLP-1 analogues. Traditionally, conformational restriction has been employed not only to stabilize structure of peptides but also to enhance their enzymatic stability. Among many cyclic GLP-1 analogues that may potentially be produced, we have focused on ones that would stabilize the receptor-bound conformation of GLP-1 since this can ensure potent receptor-binding affinity. 2D-NMR studies of GLP-1 showed that it adopts highly α-helical structure containing two helical segments between residues 13-20 and 24-35, covering more than the half of the peptide, and a linker region between residues 21-23 (25,26). Thus, a lactam bridge between a lysine at the i position and a glutamic acid at the i+4 position was used to stabilize α-helical structure where the cyclization was introduced (27), and a series of cyclic GLP-1 analogues containing such lactam bridges were synthesized to strengthen the receptor-bound structure of GLP-1 (28).

Briefly, GLP-1, D-GLP-1 (D-alanine at the $8^{th}$ position), and two bicyclic GLP-1 peptide analogues (EM2196, EM2198) were synthesized by Fmoc solid-phase chemistry, followed by the coupling of 1,4,7,10-Tetraazacyclododecane-1,4,7-tris-acetic acid-10-maleimido ethyl-acetamide (maleimido-mono-amide-DOTA to the Cys at the C-terminus of the peptides. The peptide conjugates were labeled with $^{64}Cu$ under a mild condition. The in vitro stability of the $^{64}Cu$-labeled peptides was evaluated in rat serum at 37° C. After protein precipitation with ethanol, the serum mixture was centrifuged and the supernatant was analyzed by radio-HPLC. The half maximal effective concentrations ($EC_{50}$) of the peptides were determined by the dose-response of the peptide triggered cyclic AMP (cAMP) accumulation using HEK293 cells, which stably express GLP-1R-GFP in the presence of the phosphodiesterase inhibitor 3-isobutyl-1-methylxanthine (IBMX) at 37° C. Dynamic PET/CT scans were performed on a Siemens Inveon PET-CT multimodality system using normal male BABL/c mice (n=3 per peptide). Post-PET biodistribution was performed to verify the imaging findings.

The peptide conjugates were synthesized and characterized by HPLC and MALDI-Mass spectroscopy. The specific activity of the labeled peptides was up to $6.0 \times 10^5$ Ci/mol with radiochemical purity>99%. After 1 h incubation in rat serum, all peptides showed similar stability (~50%) as determined by radio-HPLC. Compared to GLP-1 and D-GLP-1, both bicyclic peptides (EM2196 and EM2198) showed markedly higher agonistic potency in triggering cAMP accumulation ($EC_{50}$ of EM2196 and EM2198: ~1 nM; $EC_{50}$ of GLP-1: 5 nM). Dynamic PET-CT imaging revealed rapid pancreas uptake (<5 min) and high renal accumulation of $^{64}Cu$ labeled peptides in normal mice. While GLP-1, D-GLP-1, and EM2196 showed fast clearance (<10 min) from the pancreas, EM2198 demonstrated significantly longer pancreatic retention (>30 min). Post-PET biodistribution data was in agreement with the imaging findings.

The potential of a $^{64}Cu$ labeled bicyclic GLP-1 peptide for PET imaging of pancreatic β-cell mass (BCM) was analyzed and the results are shown herein below. Additional progress on specific binding and monitoring of the beta-cell mass were evaluated in STZ-induced diabetic mice.

FIG. 1 is a diagram that shows the introduction of a lactam bridge to GLP-1, and the enhanced binding obtained with the bicyclic GLP-1 analogues of the present invention. Twelve cyclic GLP-1 analogues containing lactam bridges in various regions (from the N- to C-terminal regions) were designed and synthesized. The cyclic peptides were prepared by following standard solid-phase peptide synthesis protocol with N-Fmoc/$^t$Bu protecting group strategy. The side chains of a lysine and a glutamic acid that would form a lactam bridge were protected with allyl groups which were selectively removed by using $Pd^0$ catalyst and an allyl scavenger like N,N-dimethylbarbituric acid (29). The released free amine and carboxylic acid were coupled on resin using HBTU or BOP to form a cyclic peptide. The prepared cyclic GLP-1 analogues were assessed for their receptor-binding and activation using HEK293 cells stably expressing human GLP-1 receptors, and competitive receptor binding assay of the peptides was carried out using $^{125}I$-exendin(9-39) as a radioligand in the presence of a DPP-IV inhibitor (30). In addition, cAMP formation by the peptides was determined by radioimmunoassay using the transfected HEK293 cells to examine agonistic activity. Among the twelve cyclic GLP-1 analogues, six peptides showed comparable or improved receptor-binding and activation, such as HAEGTFTSDESSYKEG-QAAKEFIAWLVKGR (SEQ ID No: 5) and HAEGTFTSD-VSSYLEGQAAKEFIEWLVKG R (SEQ ID No: 6). These cyclic GLP-1 analogues also showed enhanced stability against enzymatic degradation when assessed with isolated enzymes (DPP-IV and NEP 24.11) and kidney cells over 24 h.

Besides achieving enzymatic stability of GLP-1, several GLP-1 analogues were examined for imaging pancreatic beta-cells in vitro and in vivo. GLP-1 receptor (GLP-1R) is mainly expressed on pancreatic beta-cells but to a less extent by lung, heart, kidneys, gastrointestinal tract, or brain. While GLP-1 analogues have been extensively studied for the treatment of type 2 diabetes, none of them have been reported for non-invasive imaging of pancreatic beta-cells. Thus, four GLP-1 analogues were evaluated by in vitro binding assay and in vivo tissue distribution.

A linear GLP-1 analogue, HAEGTFTSDESSYKEG-QAAKEFIAWLVKGR (SEQ ID No: 5) was labeled with $^{125}$I (at Tyr$^{19}$). This peptide showed an appreciable specific binding to freshly isolated rat islets as determined by a displacement binding assay, the tissue distribution of the peptide in normal Sprague-Dawley rats demonstrated no significant pancreas uptake and instead high accumulation in kidneys and stomach. This presumably resulted from the degradation of the peptide by DPP-IV since it has Ala at position 8. In order to overcome this problem, we have replaced the L-Ala with a D-Ala. Furthermore, due to high stomach uptake likely resulting from in vivo de-iodination of the $^{125}$I-labeled peptide, a conventional metal chelator, DOTA (1,4,7,10-tetraaza-cyclododecane-1,4,7,10-tetraacetic acid) was conjugated to the C-terminus of GLP-1 using a cysteine (Scheme 1). Standard thiol-maleimide conjugation provided coupling of DOTA to both L-GLP-1 ([Ala$^8$]GLP-1-Ahx-Cys) SEQ ID No: 1 and D-GLP-1 ([D-Ala$^8$]GLP-1-Ahx-Cys) SEQ ID No:1, and the DOTA-GLPx1 conjugates were characterized and purified using HPLC and MALDI-MS. The purified conjugates were labeled with either $^{64}$Cu or $^{111}$In in high radiochemical yields.

Scheme 1.
Conjugation of DOTA-maleimide with GLP-1 peptides

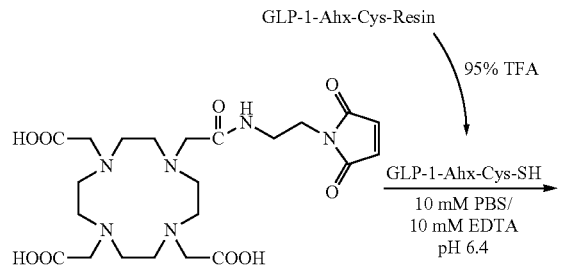

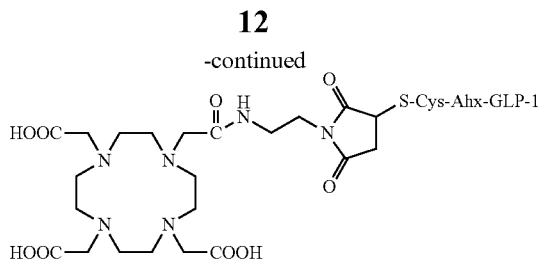

Figure 2:
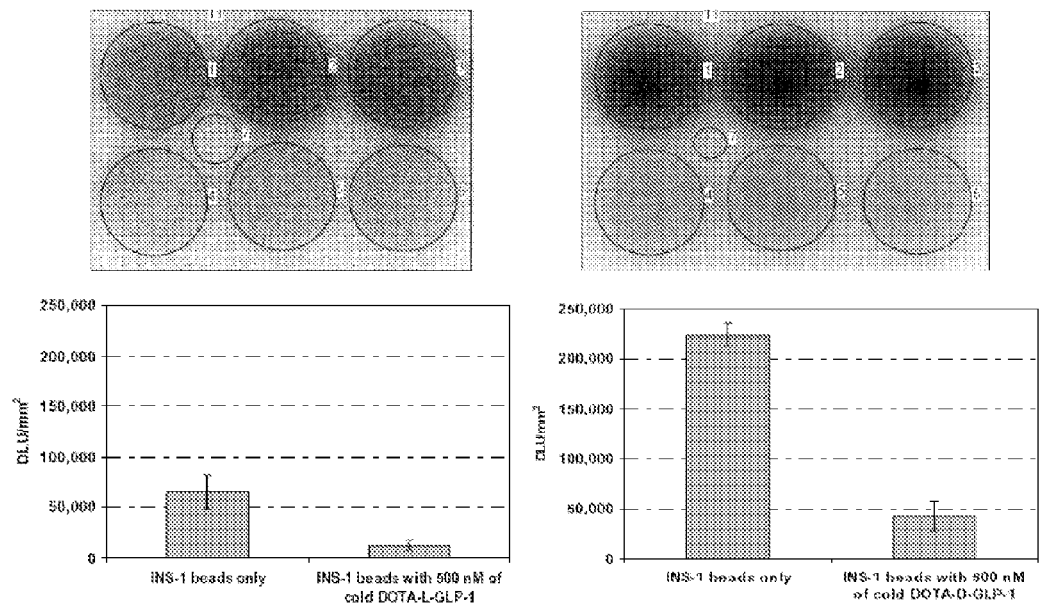
FIG. 2 shows the in vitro specific binding of GLP-1(7-36)-NH$_2$ (left) SEQ ID No: 1 and (right) SEQ ID No: 30 to INS-1 embedded collagen beads. Upper panel: autoradiography images; lower panel: semi-quantitation of the autoradiography images.

FIG. 2 shows the in vitro specific binding of L-GLP-1 (left) and D-GLP-1 (right) to INS-1 embedded collagen beads. Upper panel: autoradiography images; lower panel: semi-quantitation of the autoradiography images. For in vitro evaluation, INS-1 (an insulinoma cell line)-embedded collagen beads (~1,000 cells/bead) were used. About 6,000 beads were added to each well of a 6-well plate containing 2 mL of 10 mM PBS. For the displacement binding assay, 500 nM of the cold conjugate was present in three wells of the plate. After the addition of ca. 0.2 µCi of a radiolabeled DOTA-GLP1 conjugate to each well (calculated concentration of the radiolabeled conjugate in each well: 0.80-0.89 nM), the plate was incubated at RT over 1 h. The beads were then washed twice with 2 mL of 10 mM PBS. For autoradiography imaging, the 6-well plate was exposed to a phosphor plate, which was then read by a PerkinElmer Cyclone system. As shown in FIG. 2, both conjugates showed high specific binding to the INS-1-embedded beads (ca. 5 times of binding decrease in presence of 500 nM of a cold peptide), while the absolute uptake of the D-GLP-1 conjugate was about 4 times higher.

Given this encouraging in vitro result, the tissue distribution of both conjugates in normal Sprague-Dawley rats was examined. As summarized in Table 1, the D-GLP-1 conjugate impressively showed more than 10 times higher pancreas uptake than the L-GLP-1 conjugate at 20 min, 1 h, and 24 h post-injection (p.i.); and significantly higher contrast ratios of pancreas to the neighboring organs (pancreas/blood, pancreas/muscle, pancreas/liver, pancreas/spleen, pancreas/small intestine, pancreas/large intestine and pancreas/stomach) at all time points. However, it should be noted that both conjugates exhibited considerable kidney accumulation within the study period although the D-GLP-1 conjugate showed lower deposition in kidneys within 4 h post-injection.

TABLE 1

Biodistribution data of $^{64}$Cu-labeled DOTA-L-GLP-1 and DOTA-D-GLP-1 peptides in normal Sprague-Dawley rats (n = 4).

| % ID/g | 20-min | | 1-h | | 4-h | | 24-h | |
| --- | --- | --- | --- | --- | --- | --- | --- | --- |
| | L-GLP-1 | D-GLP-1 | L-GLP-1 | D-GLP-1 | L-GLP-1 | D-GLP-1 | L-GLP-1 | D-GLP-1 |
| blood | 0.78 ± 0.14 | 0.91 ± 0.39 | 0.47 ± 0.03 | 0.41 ± 0.07 | 0.62 ± 0.15 | 0.45 ± 0.02 | 0.07 ± 0.07 | 0.14 ± 0.08 |
| lung | 1.92 ± 0.08 | 4.03 ± 1.64 | 0.90 ± 0.14 | 0.91 ± 0.12 | 1.02 ± 0.13 | 0.77 ± 0.18 | 0.83 ± 0.18 | 1.21 ± 0.30 |
| liver | 1.13 ± 0.42 | 2.69 ± 1.16 | 2.03 ± 0.25 | 1.17 ± 0.45 | 3.34 ± 0.58 | 1.56 ± 0.14 | 1.43 ± 0.21 | 2.26 ± 0.16 |
| spleen | 0.28 ± 007 | 0.22 ± 0.05 | 0.18 ± 0.08 | 0.23 ± 0.05 | 0.40 ± 0.35 | 0.26 ± 0.20 | 0.38 ± 0.47 | 0.52 ± 0.18 |
| kidney | 30.59 ± 6.76 | 19.61 ± 0.91 | 34.27 ± 5.42 | 28.25 ± 5.83 | 41.39 ± 4.98 | 30.72 ± 9.53 | 45.76 ± 2.94 | 46.06 ± 10.89 |
| muscle | 0.12 ± 0.01 | 0.30 ± 0.15 | 0.00 ± 0.00 | 0.63 ± 0.05 | 0.00 ± 0.00 | 0.11 ± 0.13 | 0.08 ± 0.10 | 0.39 ± 0.29 |
| fat | 0.35 ± 0.10 | 0.44 ± 0.60 | 0.00 ± 0.00 | 0.28 ± 0.40 | 0.72 ± 0.57 | 0.96 ± 0.88 | 0.01 ± 0.01 | 0.78 ± 0.14 |
| heart | 0.39 ± 0.23 | 0.64 ± 0.16 | 0.11 ± 0.10 | 0.46 ± 0.21 | 0.20 ± 0.06 | 0.15 ± 0.09 | 0.00 ± 0.00 | 0.04 ± 0.05 |
| stomach | 0.64 ± 0.28 | 1.02 ± 0.51 | 0.46 ± 0.28 | 0.49 ± 0.31 | 0.50 ± 0.15 | 0.23 ± 0.07 | 0.11 ± 0.04 | 0.25 ± 0.17 |
| small int | 0.38 ± 0.21 | 1.07 ± 0.73 | 0.45 ± 0.24 | 1.02 ± 0.75 | 0.93 ± 0.43 | 0.50 ± 0.25 | 0.42 ± 0.16 | 0.91 ± 0.31 |
| large int | 0.19 ± 0.10 | 0.45 ± 0.20 | 0.04 ± 0.04 | 0.67 ± 0.70 | 0.67 ± 0.47 | 0.77 ± 0.18 | 4.83 ± 1.16 | 2.01 ± 0.02 |
| pancreas | 0.34 ± 0.14 | 3.58 ± 0.56* | 0.11 ± 0.11 | 2.19 ± 0.98* | 0.40 ± 0.56 | 1.18 ± 0.12* | 0.03 ± 0.06 | 0.99 ± 0.05* |
| P/blood | 0.43 | 3.92 | 0.24 | 5.40 | 0.64 | 2.60 | 0.50 | 7.29 |
| P/muscle | 2.81 | 12.02 | n.a. | 3.49 | n.a. | 11.22 | 0.42 | 2.56 |
| P/liver | 0.30 | 1.33 | 0.056 | 1.87 | 0.12 | 0.76 | 0.02 | 0.44 |

TABLE 1-continued

Biodistribution data of $^{64}$Cu-labeled DOTA-L-GLP-1 and DOTA-D-GLP-1 peptides in normal Sprague-Dawley rats (n = 4).

| | 20-min | | 1-h | | 4-h | | 24-h | |
|---|---|---|---|---|---|---|---|---|
| % ID/g | L-GLP-1 | D-GLP-1 | L-GLP-1 | D-GLP-1 | L-GLP-1 | D-GLP-1 | L-GLP-1 | D-GLP-1 |
| P/spleen | 1.21 | 16.09 | 0.61 | 9.47 | 0.99 | 4.61 | 0.09 | 1.91 |
| P/stomach | 0.53 | 3.53 | 0.24 | 4.45 | 0.80 | 5.18 | 0.31 | 3.98 |
| P/sm int | 0.88 | 3.36 | 0.25 | 2.14 | 0.43 | 2.36 | 0.07 | 1.09 |
| P/lg int | 1.79 | 7.96 | 2.75 | 3.27 | 0.60 | 1.53 | 0.006 | 0.49 |

Data are presented as % ID/g ± s.d. (% ID/g: percentage of injected dose per gram of tissue; P: pancreas; int: intestine; sm: small; lg: large;
*statistically significant ($p < 0.05$)).

In addition, the biodistribution results revealed the peptide accumulation only in the pancreas. As shown in the in vitro results (FIG. 2, it is reasonable to assume that the elevated pancreas uptake of the D-GLP-1 conjugate resulted from the specific beta-cell targeting. However, in order to verify the specific deposition and correlate biodistribution or imaging results with the beta-cell mass, islets of Langerhans were isolated post-biodistribution or PET imaging.

Synthesis and characterization of enzymatically stable GLP-1 analogues and multivalent metal-chelating scaffolds.

Enzymatically stable GLP-1 analogues: The stability of GLP-1 analogues affects in vivo imaging. In order to achieve such peptides, a series of cyclic GLP-1 analogues were designed and synthesized that include lactam bridges between $Lys^i$ and $Glu^{i+4}$ and which stabilize the α-helical structure in GLP-1 (28). Among them, a number of cyclic peptides were found to have comparable or improved receptor-binding and activation, and showed moderate enzymatic stability when incubated with kidney cells. These cyclic peptides are:

```
                                    SEQ ID NO: 5
HAEGTFTSDESSYKEGQAAKEFIAWLVKGR (1C),

SEQ ID NO: 13
HAEGTFTSDVSEYLEKQAAKEFIAWLVKGR (2C),

SEQ ID NO: 31
HAEGTFTSDVSSYLEKQAAEEFIAWLVKGR (3C),

SEQ ID NO: 32
HAEGTFTSDVSSYLEGKAAKEFIAWLVKGR (4C),

SEQ ID NO: 33
HAEGTFTSDVSSYLEGQAAKEFIEWLVKGR (5C),
and
                                    SEQ ID NO: 34
HAEGTFTSDVSSYLEGQAAKEFIKWLVEGR (6C).
```

Despite their high potency ($EC_{50}$=1-10 nM), all of the cyclic peptides (1C-6C) possess $Ala^8$-$Glu^9$ sequence, which is highly susceptible to DPP-IV digestion. This suggests that the mono-cyclization will not be sufficient to provide significant enzymatic stability. Thus, in order to prevent the metabolism by DPP-IV, D-Ala at position 8 was used. The D-Ala$^8$ substitution was found not to affect receptor binding (31) and provides increased stability over DPP-IV.

However, it should be noted that DPP-IV is not the only enzyme responsible for the metabolism of GLP-1. Compared to DPP-IV, neutral endopeptidase (NEP 24.11) cleaves multiple sites in GLP-1 and the cleavage sites are $Asp^{15}$-$Val^{16}$, $Ser^{18}$-$Tyr^{19}$, $Tyr^{19}$-$Leu^{20}$, $Glu^{27}$-$Phe^{28}$, $Phe^{28}$-$Ile^{29}$, and $Trp^{31}$-$Leu^{32}$ (32). Since all of these sites are within the sequences stabilized by the lactam bridges in 1C-6C, the cyclization via the lactam bridge provides sufficient stabilization over NEP 24.11. But, in order to maximize the enzymatic stability, bicyclic GLP-1 analogues were synthesizes that protect against NEP 24.11. Using the six cyclizations (1C-6C), nine bicyclic GLP-1 analogues were made: 1C/3C (BC1), 1C/4C (BC2), 1C/5C (BC3), 1C/6C (BC4), 2C/4C (BC5), 2C/5C (BC6), 2C/6C (BC7), 3C/6C (BC8), and 4C/6C (BC9). These nine bicyclic GLP-1 analogues (BC1-BC9) were synthesized using the standard solid-phase peptide synthesis technique as successfully used in the preparation of the cyclic GLP-1 analogues. Each of the bicyclic peptides has D-Ala$^8$ for DPP-IV stability and a cysteine at the C-terminus for conjugating to a multivalent metal chelator via an aminohexanoic acid as a spacer. The bicyclic structure and D-Ala$^8$ substitution provided substantial enzymatic stability to facilitate beta-cell imaging. For the construction of a bicyclic GLP-1 analogue, a linear peptide of which sequence contains only the first lactam bridge was grown on solid support using Fmoc-protected amino acids. For the first on-resin cyclization, allyl protecting groups on a Lys and a Glu that are to form the first lactam bridge were removed selectively and the released free amine and carboxylic acid were coupled to form a monocyclic peptide. By repeating these steps, a bicyclic GLP-1 analogue were constructed and assessed for its receptor-binding and activation.

In vitro evaluation of $^{64}$Cu-labeled GLP-1 constructs: The stability of radiolabeled GLP-1 constructs was determined in vitro by incubation at 37° C. in fresh mammalian serum up to 24 h. The volume of a radiolabeled construct added did not exceed 5% of the total volume. Degradation of the radiolabeled constructs was assessed at given time points by the removal of an aliquot of sample for radio-TLC ($C_{18}$ or silica gel solid phase) or radio-HPLC ($C_{18}$ and size-exclusion columns) analysis. On radio-HPLC, radioactivity that is not associated with an intact construct is a measure of the enzymatic degradation.

In vitro autoradiography evaluation of $^{64}$Cu-labeled GLP-1 constructs: The radiolabeled GLP-1 constructs were incubated with INS-1-embedded collagen beads with and without their cold counterparts, and the remaining radioactivity was measured after washing. Radiolabeled GLP-1 constructs in vivo using normal and diabetic animal models.

Biodistribution of $^{64}$Cu-labeled GLP-1 constructs in normal Sprague-Dawley rats: Tissue distribution of selected radiolabeled GLP-1 constructs was performed with normal Sprague-Dawley rats. The radiolabeled compounds were diluted with saline and be injected into rats (n=4 at each time point) via the tail vein. The animal number at each time point was chosen for statistical analysis. Time points were selected according to the physical half-life of $^{64}$Cu (20 min, 1 h, 4 h, and 24 h). At the selected post-injection time points, animals were sacrificed, and organs of interest removed, weighed, and counted. The percent injected dose per gram (% ID/g) and percent injected dose per organ (% ID/organ) was calculated by comparison to a weighed, counted standard. Pharmacokinetic parameters were estimated by using either one- or two-compartment model. Specifically, blood (10-20 µL) was drawn from the animals at 5, 10, 20, and 40 min, and counted on a gamma counter.

Urine excretion experiments were carried out with the last time point animal groups. Rat urine was collected from metabolic cages at selected time points post-injection. In addition, the urine was concentrated under nitrogen so that radio-TLC or radio-HPLC analysis can be performed to determine the percentage of intact peptide conjugates.

Biodistribution of $^{64}$Cu-labeled GLP-1 constructs in Streptozotocin-induced diabetic rats: Type 1 diabetic rats were established by administering streptozotocin (STZ; 65 mg/kg in 20 mM citrate saline buffer) intraperitoneally (i.p.) to mature Sprague-Dawley rats fasted for two days (40-42). The biodistribution procedures were the same as above, but only one time point that showed the highest pancreas uptake was selected. Histomorphometry of pancreas and islets were performed after the dissection to determine the percentage of beta-cell fraction in the rat's pancreas with established methods (43-46).

PET imaging evaluation of selected $^{64}$Cu-labeled GLP-1 constructs in diabetic rats: Many GLP-1 constructs with a positive pancreas uptake and beta-cell density correlation were evaluated using PET imaging. Type 1 diabetes rat model were used: The biobreeding diabetes-prone (BB-DP) rats available from Biomedical Research Models Inc. (Worcester, Mass.) spontaneously develop type 1 diabetes with an average onset of hyperglycemia at 10 weeks of age. Blood glucose levels and the area under the curves of the intraperitoneal glucose tolerance test (AUC IPGTT) were monitored daily and twice a week from the rat's age of 50 days, respectively, by established methods (46-48). Blood samples (~10 µL) were collected from the tail veins of 4 h-fasted rats. The IPGTTs were performed in fasting unanesthetized animals. After the measurement of baseline blood glucose, animals received an i.p. injection of 2 g/kg glucose. The blood glucose levels were measured at 30, 60, 90, and 120 min after the glucose injection.

Example 1

Enzymatically Stable GLP-1 Analogues for Imaging Pancreatic Beta-Cells

A series of cyclic GLP-1 analogues to determine the receptor-bound conformation of GLP-1. In this example, a lactam bridge between Lys$^i$ and Glu$^{i+4}$ was employed to stabilize an α-helical structure in various regions of GLP-1 and was demonstrated that a strategically positioned conformational restriction can enhance interaction with the receptor.

To achieve GLP-1 analogues with high receptor affinity and enzymatic stability, we have placed two lactam bridges between Glu$^i$ and Lys$^{i+4}$ to simultaneously stabilize α-helical structures in the N- and C-terminal regions of GLP-1. In addition, D-Ala$^8$ was also introduced to prevent the degradation by DPP-IV. The resulting bicyclic GLP-1 analogues were examined by cAMP production assays to determine receptor interaction and also studied for enzymatic stability against DPP-IV and NEP. After conjugated to DOTA, bicyclic GLP-1 analogues were labeled with $^{64}$Cu and dynamic PET/CT scans were carried out on a Siemens Inveon PET-CT multi-modality system using normal mice.

Peptide Synthesis:

Bicyclic GLP-1 analogues were synthesized by using standard Fmoc/t-butyl solid-phase peptide chemistry. For an on-resin lactam bridge formation, Glu(OAl) and Lys(Aloc) were introduced in a linear peptide and the allyl protecting groups were selectively removed by using Pd$^0$, followed by cyclization with PyBOP. The resulting crude peptides were purified by RP-HPLC and characterized by ESI-MS.

cAMP Production Assay: Cyclic AMP accumulation was determined in subconfluent cultures of HEK293 cells stably expressing GLP-1R in the presence of the phosphodiesterase inhibitor 3-isobutyl-1-methylxanthine (IBMX) For dose-response experiments, cells were treated with a peptide for 20 min. at 37° C. In all cases, reactions were stopped with 1.2 M trichloroacetic acid and cAMP was isolated by the two column chromatographic method.

Enzymatic Degradation: (A) DPP-IV [4]: A peptide (100 µM) was incubated with DPP-IV (0.2 ng/mL) at 37° C. in Tris buffer (25 mM, pH 8.0). At the time of 0, 2, 4, 6, 9, and 24 h, an aliquot (100 µL) was taken out and quenched with aqueous TFA (10%, 20 µL) and analyzed by RP-HPLC (10-90% CH$_3$CN in water (0.1% TFA) over 40 min; flow rate, 1.0 mL/min; C18-bonded Zorbax column, 4.6×250 mm).

(B) NEP 24.11 [5]: A peptide (50 µM) was incubated with NEP 24.11 (20 ng/mL) at 37° C. in HEPES buffer (50 mM, pH 7.4, 50 mM NaCl). At the time of 0 and 24 h, an aliquot (100 µL) was taken out and quenched with aqueous TFA (10%, 20 µL) and analyzed by RP-HPLC.

Figure 4:
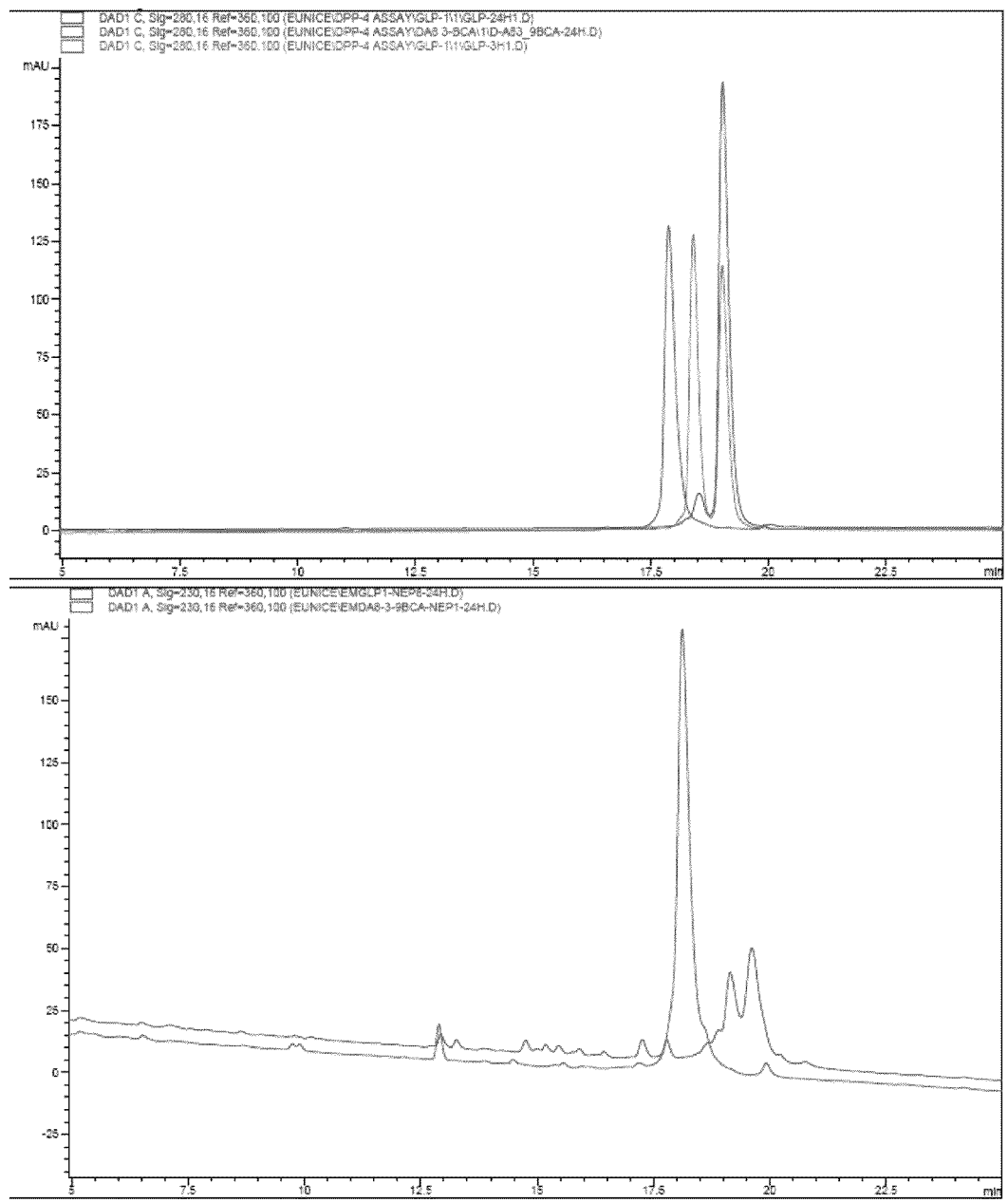
FIG. 4 are HPLC chromatograms of a bicyclic GLP-1 analogue after incubation with DPP-IV and NEP, Green, GLP-1(7-36)-NH$_2$(3 h) SEQ ID No: 1; Blue, GLP-1(7-36)-NH$_2$ (24 h) SEQ ID No: 1, Red, HXEGTFTSDVSEYLEKQAAKEFIEWLVKGR, wherein X is D-Ala (SEQ ID No: 12) (24 h) (EM2198).
Figure 5:
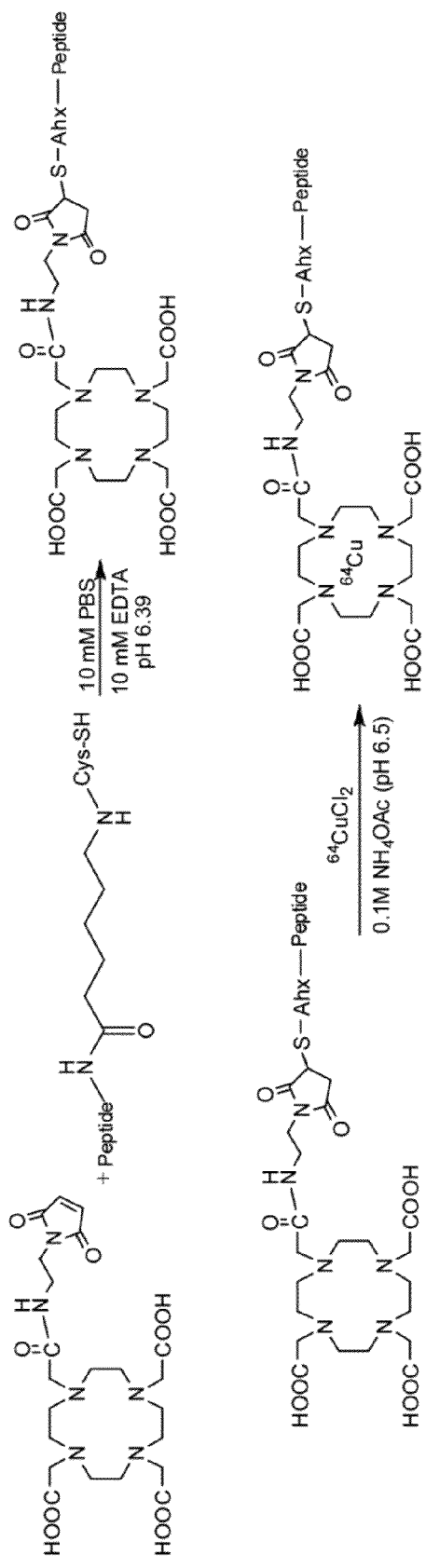
FIG. 5 is the Synthesis of a PET imaging agent by using a bicyclic GLP-1 analogue.
Figure 6:
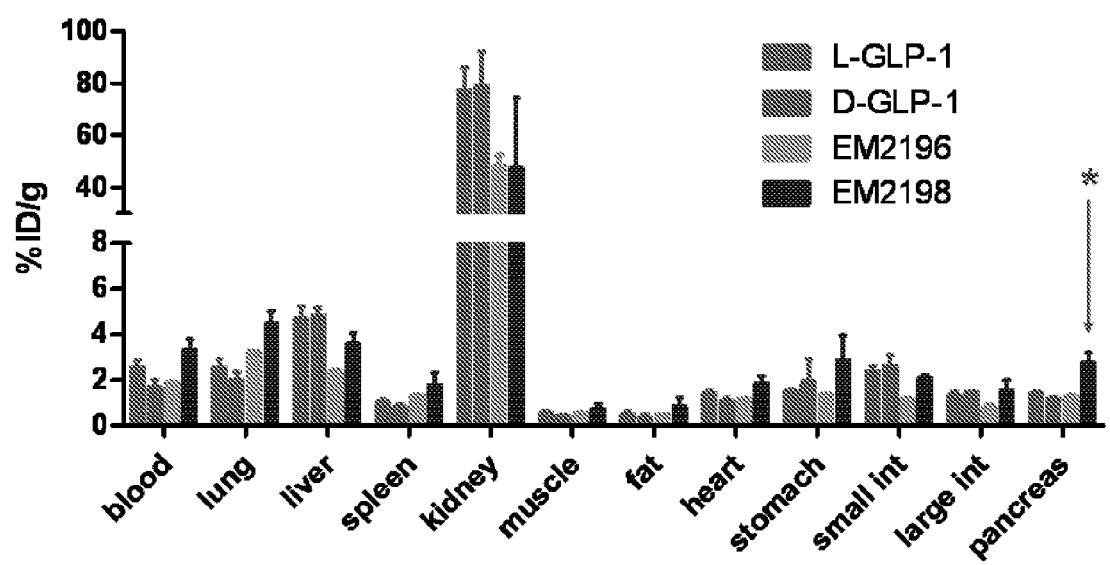
FIG. 6 is a graph that shows the binding of L-GLP-1 (GLP-1(7-36)-NH2) SEQ ID No: 1, D-GLP-1 ([D-Ala8]GLP-1(7-36)-NH$_2$) SEQ ID No: 30, EM2196 HXEGTFTSDESSYKEGQAAKEFIEWLVKG R, wherein X is D-Ala, (SEQ ID No: 11) and EM2198 HXETFTSDVSEYLEKQAAKEFIEWLVKQ R, wherein X is D-Ala, (SEQ ID No: 12) to various organs.
Figure 7:
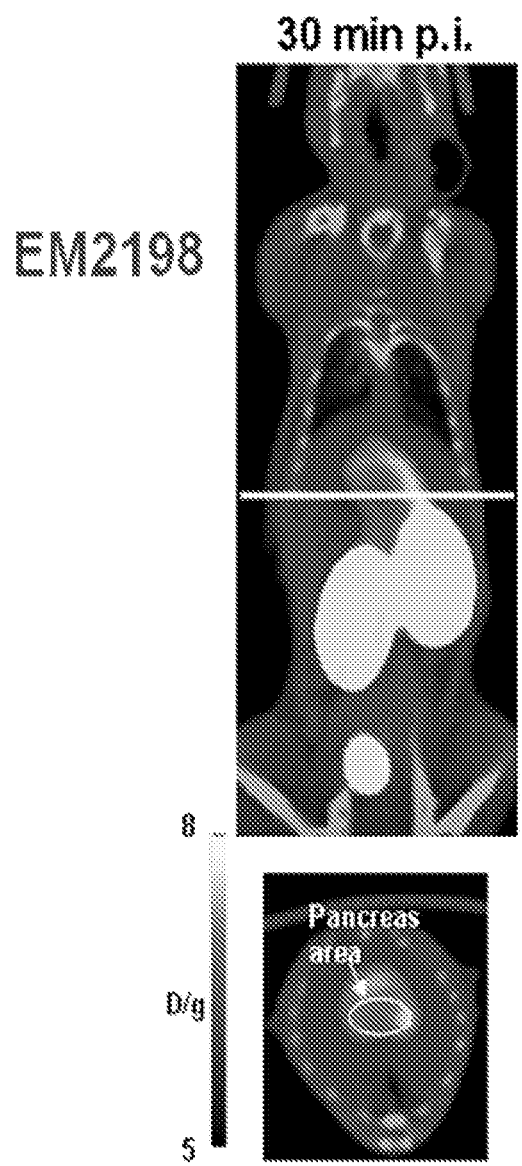
FIG. 7 is a PET image of the binding of EM2198 in a mouse.

FIG. 3 is a chart that shows receptor activation by cyclic GLP-1 analogues. FIG. 4 are HPLC chromatograms of a bicyclic GLP-1 analogue after incubation with DPP-IV and NEP, Green, GLP-1(7-36)-NH$_2$(3 h) SEQ ID No: 1; Blue, GLP-1(7-36)-NH$_2$(24 h) SEQ ID No: 1, Red, HXEGTFTS-DESSYKEGQAAKEFIEWLVKGR, wherein X is D-Ala, (SEQ ID No: 11). FIG. 5 is the synthesis of a PET imaging agent by using a bicyclic GLP-1 analogue. FIG. 6 is a graph that shows the binding of L-GLP-1, D-GLP-1, EM2196 and EM2198 to various organs. FIG. 7 is a PET image of the binding of EM2 198 in a mouse.

Figure 8:
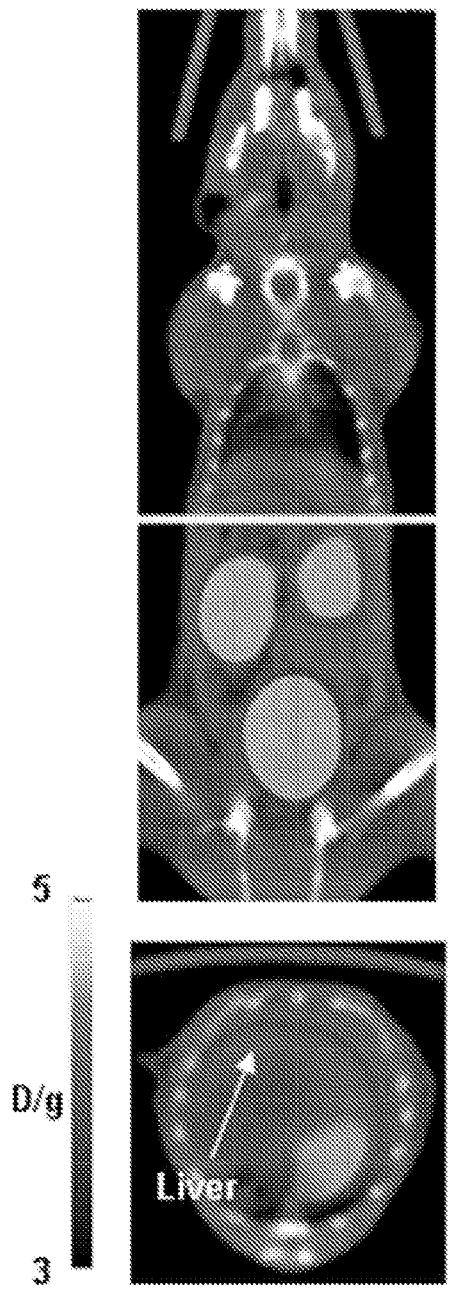
FIG. 8 is a PET image of the binding of EM2198 in a mouse with blocking with Exendin-4.
Figure 9:
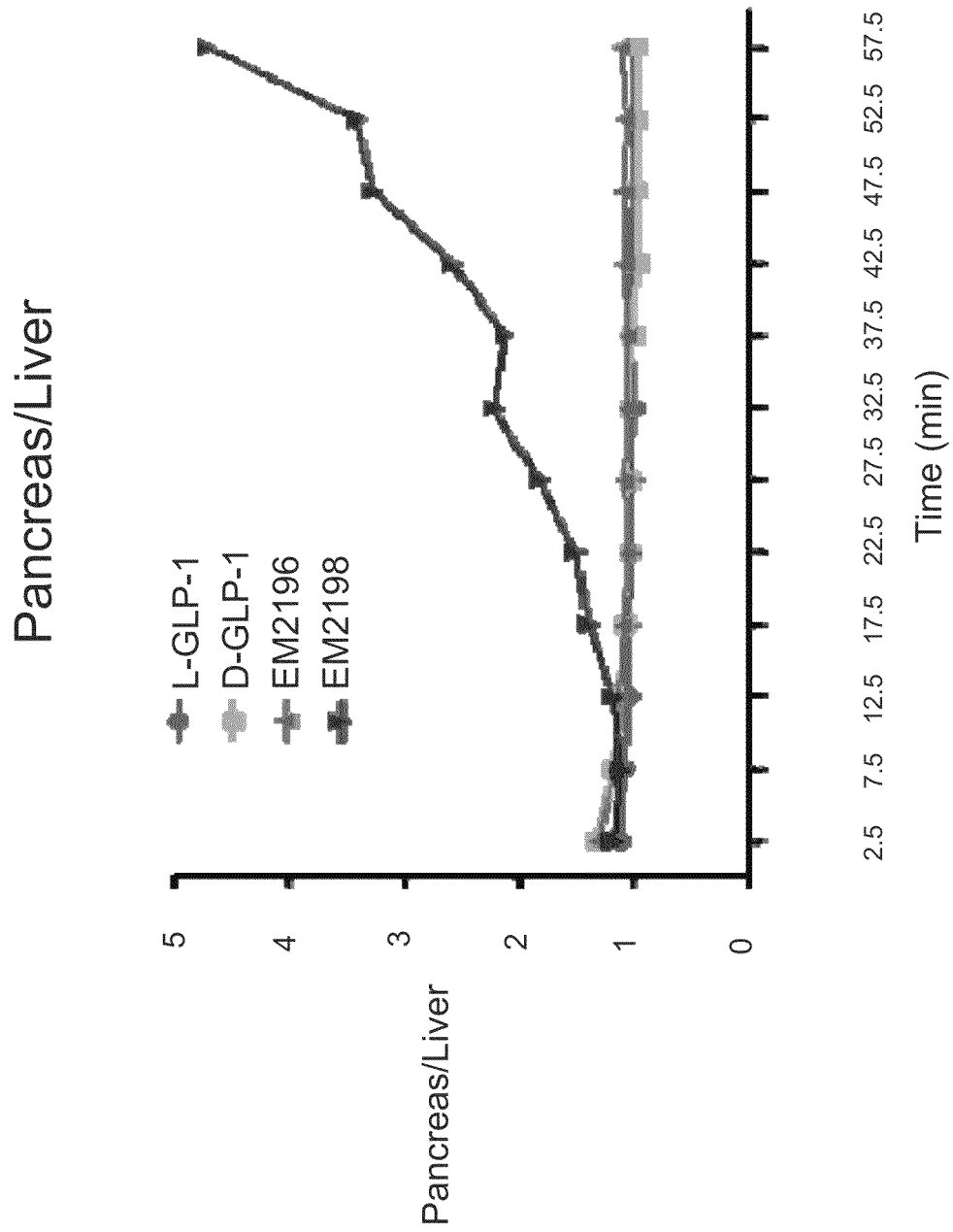
FIG. 9 is a graph that shows the contrast in pancreatic and liver microPET scans.
Figure 10:
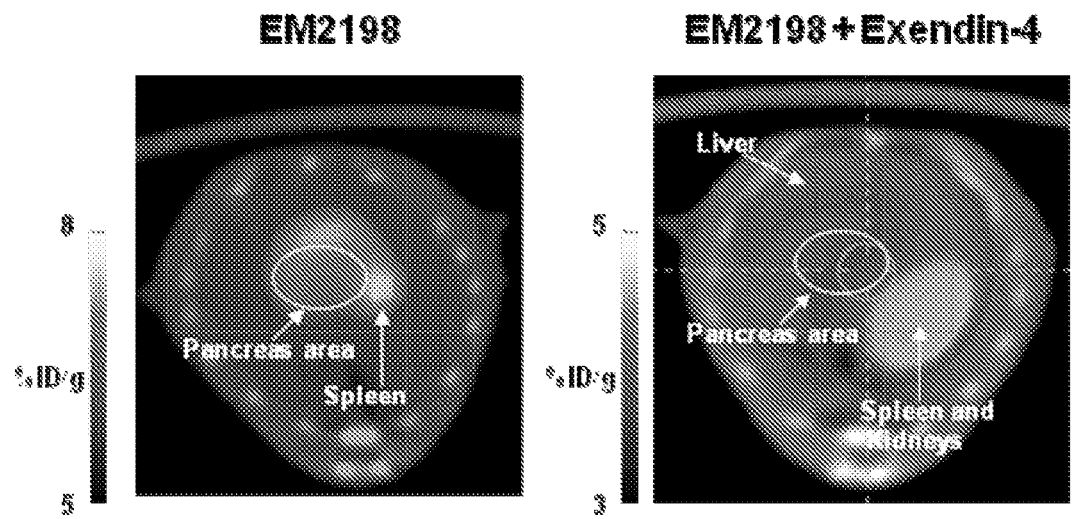
FIG. 10 are transaxial PET/CT images at 30 min p.i. of EM2198 with or without exendin-4 blocking
Figure 11:
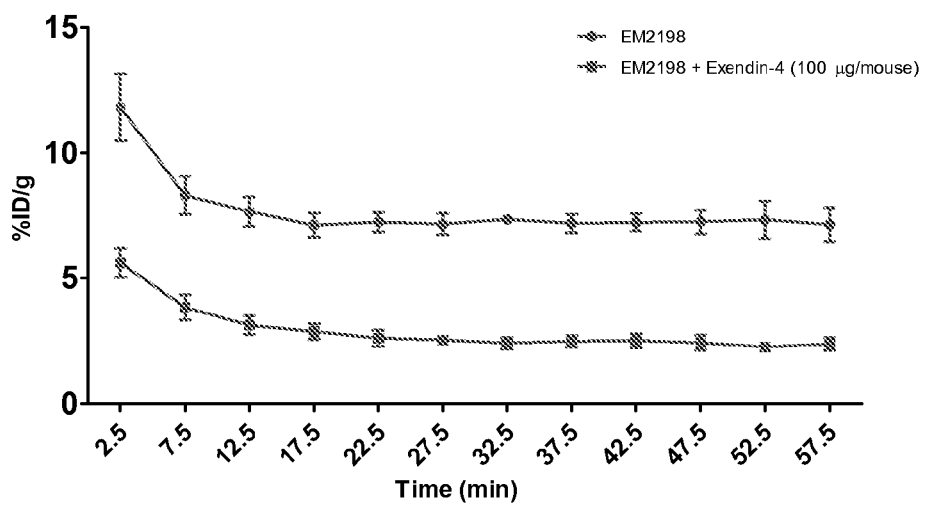
FIG. 11 is a graph that shows that EM2198 specifically target the GLP-1R in pancreas.
Figure 12:
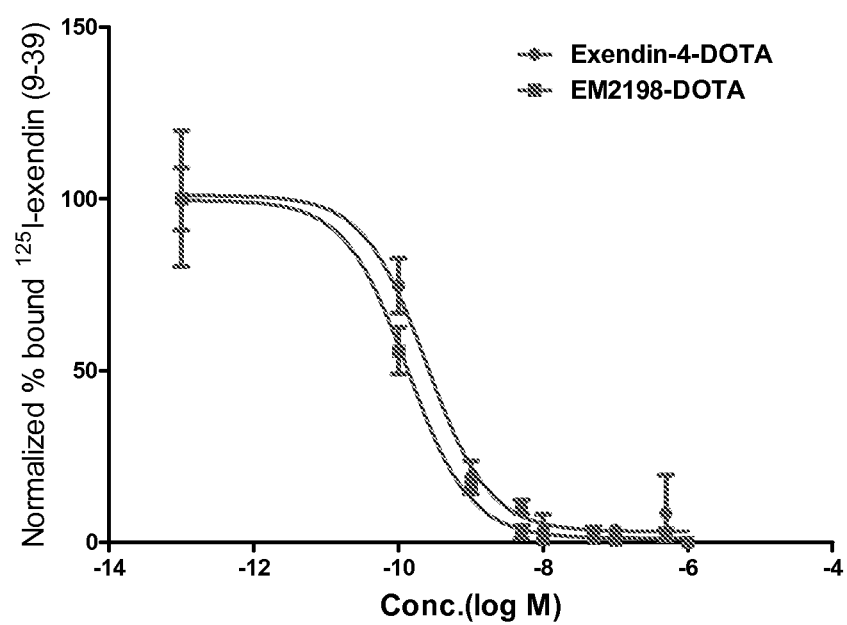
FIG. 12 is a graph that illustrates binding of the Exendin-4 to target GLP-1 receptors.

FIG. 8 is a PET image of the binding of EM2198 with the addition of Extendin-4 in a mouse. microPET/CT Scans of $^{64}$Cu-EM2198 co-injected with Exendin-4 (100 µg/mouse). FIG. 9 are graphs that show a comparison of contrast in pancreatic, liver and kidney microPET scans. FIG. 10 is a transaxial PET/CT images at 30 min p.i. of EM2198 with or without exendin-4 blocking Based on the quantitative analysis of microPET/CT images, EM2198 showed the highest pancreas contrast. Its GLP-1R binding specificity was confirmed by a blocking imaging study using exendin-4. FIG. 11 is a graph that shows that EM2198 specifically target the GLP-1R in pancreas. Quantitative analysis based on micro-PET/CT 0-60 min dynamic scans, animal model: Normal BABL/c mice at 6-8 wks. Based on the quantitative analysis of microPET/CT images, EM2198 showed the highest pancreas contrast. Its GLP-1R binding specificity was confirmed by a blocking imaging study using exendin-4. FIG. 12 is a graph that illustrates binding of the bicyclic GLP-1 analogue (EM2198) and Exendin-4.

The present invention also provides a novel Exendin-4 biomarker. To develop effective molecular imaging probes, novel cyclic Exendin-4 analogues (as well as noncyclic Exendin-4 analogues) were designed and synthesized and proved to show significantly improved stability against enzymatic degradation. In addition, the cyclic structure enhanced the potency of the cyclic Exendin-4 analogues that allowed clear detection of pancreatic beta-cells. The Exendin-4 sequence includes: HGEGTFTSDLSKQMEEEAVR-LFIEWLKNGGPSSGAPPPS (SEQ ID No: 21) as well as variations and modifications thereof, in addition, Exendin-4 sequence may be substituted and modified to be similar (having 75, 80, 85, 90, 95, 98 or 99% homology) to the Exendin-4 sequence above.

The development of these novel cyclic Exendin-4 analogues as molecular imaging agents allows early detection of, e.g., diabetes; easy monitoring of the progress of the disease; and facile evaluation of therapeutic treatment of the disease. Thus, this is of great value to pre-diabetic patients who show high potential to become diabetic for early detection and early treatment; and diabetic patients who are already diagnosed and taking medications to determine the effectiveness of drugs.

The novel cyclic Exendin-4 analogues can be labeled with proteins, radionuclides, fluorescent labels, metals, chromogenic agents, enzymes and other agents that enhace its use as an imaging agents. Examples of radionuclides include, e.g., $^{18}F$, $^{68}Ga$, $^{60/61/62/64}Cu$, $^{89}Zr$, $^{86}Y$, $^{124}I$, $^{99m}Tc$, $^{111}In$, $^{67}Ga$, $^{125}I$, $^{123}I$, $^{177}Lu$, $^{166}Ho$, and $^{153}Sm$. The imaging agent further includes at least one of a radiolabel, an enzyme, a fluorescent label, a luminescent label, a bioluminescent label, a magnetic label, and biotin. The agent further comprises at least one of an anti-metabolite, an alkylating agent, an antibiotic, a growth factor, a cytokine, an anti-angiogenic agent, an anti-mitotic agent, an anthracycline, toxin, and an apoptotic agent. The imaging agent may include or more labels that make the agent detectable by positron emission tomography (PET), single photon emission computed tomography (SPECT), radioscintigraphy, magnetic resonance imaging (MRI) and computed tomography (CT scan). The agents disclosed herein have been found to have increased resistance to proteolytic cleavage by dipeptidyl peptidase-IV (DPP-IV), neutral endopeptidase (NEP), or both.

Exendin-4, found in the venom of the Gila Monster (*Heloderma suspetum*), is also an agonist for the GLP-1 receptor (GLP-1R). It is resistant to DPP IV digestion and, unlike GLP-1, it can be truncated by 8 amino acid residues at its N-terminus without losing receptor affinity. However, the loss of the first 2-8 amino acid residues results in the generation of antagonists. The N-terminal region of GLP-1 and exendin-4 are almost identical, a significant difference being the second amino acid residue, alanine in GLP-1 and glycine in Exendin-4, which gives Exendin-4 its resistance to DPP-IV digestion. Exendin-4 has an extra 9 amino acid residues at its C-terminus which have been shown to form a 'Trp-cage' by NMR. NMR analysis of Exendin-4 also shows that the central region (amino acid residues 10-30) is helical in structure. Interestingly GLP-1 and Exendin-4 only share 8 amino acid residues in this region but since they lie on the same face of the α-helix, we postulate that this face of the helix interacts with the receptor.

The GLP-1 receptor (GLP-1R) has been cloned and is a member of the 'family B' G protein-coupled receptors (GPCRs). Other members of this family include receptors for glucagon, calcitonin, glucose-dependent insulinotropic polypeptide and vasoactive intestinal peptide. It is known that the large amino terminal domain that characterizes the 'family B' GPCRs plays a key role in ligand binding. However, the amino terminus is not entirely sufficient to bind the ligand and regions in the exctracellular loops and/or transmembrane helices are also believed to provide additional interactions.

Among many molecules that interact with pancreatic beta-cells, Exendin-4 is another ideal candidate to be employed for non-invasive imaging of the beta-cells. With recent technical innovations in various imaging modalities, molecular imaging is gaining significant attention in the basic biomedical sciences and in clinical research and practice. Indeed, non-invasive imaging techniques are revolutionizing the understanding of diseases at the cellular and molecular levels. The ability to non-invasively visualize pancreatic beta-cells would greatly facilitate the development of new methods in the prevention and treatment of diabetes. Conventional magnetic resonance imaging (MRI) and computed tomography (CT) can be used to delineate the location of the pancreas in a subject at a spatial resolution of <100 μm. However, it is extremely difficult if not impossible, for these two modalities to differentiate the islets of Langerhans from other pancreatic tissues because pancreas is a highly vascularized soft organ and the islets only represent 2-3% of the pancreatic tissues. In order to visualize the beta-cells in the islets of Langerhans, imaging or contrast agents that recognize the scarcely dispensed beta-cells within pancreas and are responsive to their biological functions, must be developed.

Among currently available imaging modalities, tomographic nuclear imaging approaches, especially positron emission tomography (PET), have demonstrated their significant importance and promising potential in applications of molecular imaging probes due to the superior sensitivity and specificity in diverse subjects, and the ability to quantitatively analyze the regions of interest.

Exendin-4, a 39 amino acid peptide originally isolated from the oral secretions of the lizard *Heloderma suspectum*, has been shown to share certain activities with glucagon-like-peptide-1 (GLP-1), a 30 amino acid peptide. Among many peptides known to interact with pancreatic beta-cells, glucagon-like peptide-1 (GLP-1) and Exendin-4 play a critical role in the function of beta-cells. Exendin-4 includes the sequence: DLSKQMEEEAVRLFIEWLKNGGPSSGAPPPS (SEQ ID NO: 3) and also may include Exendin-4 constructs (1-39, 4-39, 9-39, 1-30, 4-30, 9-30 or any variation thereof). Other Exendin-4 constructs may be used as well as other variations and mutations of Exendin. In addition, other variants of Exendin may be used including exendin-4 HSDGTFTSDLSKQMEEEAVR-LFIEWLKNGGPSSGAPPPS (SEQ ID No 4). The present invention includes Exendin constructs with similar modifications, substitutions, and construct sequences as illustrated herein for glucagon-like peptide-1 (GLP-1).

The present invention discloses an imaging composition of an cyclic analog uses a linker to connect a portion of a peptide or protein that binds specifically to the GLP-1 receptor (GLP-1R) and the cyclic analog has one or more conformational restrictions including, but not limited to, lactam bridges, disulfide bridges, hydrocarbon bridges, and their combinations, salts and derivatives thereof wherein the cyclic analog is more stable than a non-cyclic analog when incubated in the presence of enzymes that degrade GLP-1 and have an increased serum half-live to an imaging molecule.

The composition of the instant invention can be divided into three regions, a GLP-1R-binding peptide, a linker (or spacer), and a metal chelator (cyclic or linear). For example the linker molecule may be 6-aminohexanoyl-cysteine or the thiol of the cysteine to make a covalent bond with DOTA (or NOTA)-maleimide. However, the skilled artisan will know other linkers may be used. For example, the linker may include alpha-amino acids, omega-amino acids (e.g., beta-alanine, 4-aminobutyric acid, 5-aminovaleric acid, 6-aminohexanoic acid), 4-aminocyclohexanecarboxylic acid, 3-aminocyclohexanecarboxylic acid, 2-aminocyclohexanecarboxylic acid, 3-aminocyclopentanecarboxylic acid, 2-aminocyclopentanecarboxylic acid, 4-aminobenzoic acid, 3-aminobenzoic acid, 2-aminobenzoic acid, poly(ethylene glycol). The metal chelator may be HYNIC, Bolton-Hunter moiety, cross-bridged DOTA and TETA (CB-DO2A and CB-TE2A) NOTA, and DTPA. The present invention also provide different combination of peptide, linkers and metal chelators It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. National Diabetes Fact Sheet, the American Diabetes Association. www.diabetes.org/diabetes-statistics.jsp.
2. Rowland, D. J.; Lewis, J. S.; Welch, M. J., Molecular imaging: the application of small animal positron emission tomography. *J. Cell. Biochem. Suppl.* 2002, 39, 110-115.
3. Weissleder, R., Scaling down imaging: molecular mapping of cancer in mice. *Nat. Rev. Cancer* 2002, 2, 11-18.
4. Rogers, B. E.; Bigott, H. M.; McCarthy, D. W.; Della Manna, D.; Kim, J.; Sharp, T. L.; Welch, M. J., MicroPET imaging of a gastrin-releasing peptide receptor-positive tumor in a mouse model of human prostate cancer using a $^{64}$Cu-labeled bombesin analogue. *Bioconjugate Chem.* 2003, 14, 756-763.
5. West, C. M.; Jones, T.; Price, P., The potential of positron-emission tomography to study anticancer-drug resistance. Nat. Rev. Cancer 2004, 4, 457-469.
6. Mori, T., Cancer-specific ligands identified from screening of peptide-display libraries. Curr. Pharm. Des. 2004, 10, 2335-2343.
7. Stefanidakis, M.; Koivunen, E., Peptide-mediated delivery of therapeutic and imaging agents into mammalian cells. Curr. Pharm. Des. 2004, 10, 3033-3044.
8. Kieffer, T. J.; Habener, J. F., The glucagon-like peptides. Endocr. Rev. 1999, 20, 876-913.
9. Drucker, D. J., Glucagon-like peptides. Diabetes 1998, 47, 159-169.
10. Holst, J. J., Enteroglucagon. Annu. Rev. Physiol. 1997, 59, 257-271.
11. Weir, G. C.; Mojsov, S.; Hendrick, G. K.; Habener, J. F., Glucagonlike peptide I (7-37) actions on endocrine pancreas. Diabetes 1989, 38, 338-342.
12. Holst, J. J., Therapy of type 2 diabetes mellitus based on the actions of glucagon-like peptide-1. Diabetes Metab. Res. Rev. 2002, 18, 430-441.
13. Egan, J. M.; Bulotta, A.; Hui, H.; Perfetti, R., GLP-1 receptor agonists are growth and differentiation factors for pancreatic islet beta cells. Diabetes/Metab. Res. Rev. 2003, 19, 115-123.
14. Stoffers, D. A.; Kieffer, T. J.; Hussain, M. A.; Drucker, D. J.; Bonner-Weir, S.; Habener, J. F.; Egan, J. M., Insulinotropic glucagon-like peptide 1 agonists stimulate expression of homeodomain protein IDX-1 and increase islet size in mouse pancreas. Diabetes 2000, 49, 741-748.
15. Komatsu, R.; Matsuyama, T.; Namba, M.; Watanabe, N.; Itoh, H.; Kono, N.; Tarui, S., Glucagonostatic and insulinotropic action of glucagonlike peptide I-(7-36)-amide. Diabetes 1989, 38, 902-905.

16. Wettergren, A.; Wojdemann, M.; Holst, J. J., Glucagon-like peptide-1 inhibits gastropancreatic function by inhibiting central parasympathetic outflow. Am. J. Physiol. 1998, 275, G984-G992.
17. Wettergren, A.; Schjoldager, B.; Mortensen, P. E.; Myhre, J.; Christiansen, J.; Holst, J. J., Truncated GLP-1 (proglucagon 78-107-amide) inhibits gastric and pancreatic functions in man. Dig. Dis. Sci. 1993, 38, 665-673.
18. Turton, M. D.; O'Shea, D.; Gunn, I.; Beak, S. A.; Edwards, C. M.; Meeran, K.; Choi, S. J.; Taylor, G. M.; Heath, M. M.; Lambert, P. D.; Wilding, J. P.; Smith, D. M.; Ghatei, M. A.; Herbert, J.; Bloom, S. R., A role for glucagon-like peptide-1 in the central regulation of feeding. Nature 1996, 379, 69-72.
19. Larsen, P. J.; Vrang, N.; Tang-Christensen, M., Central pre-proglucagon derived peptides: opportunities for treatment of obesity. Curr. Pharm. Des. 2003, 9, 1373-1382.
20. Thorens, B., Expression cloning of the pancreatic beta cell receptor for the gluco-incretin hormone glucagon-like peptide 1. Proc. Natl. Acad. Sci. U.S.A. 1992, 89, 8641-8645.
21. Widman, C.; Dolci, W.; Thorens, B., Heterologous desensitization of the glucagon-like peptide-1 receptor by phorbol esters requires phosphorylation of the cytoplasmic tail at four different sites. J. Biol. Chem. 1996, 271, 19957-19963.
22. Widman, C.; Dolci, W.; Thorens, B., Internalization and homologous dessensitization of the GLP-1 receptor depend on phosphorylation of the receptor carboxyl tail at the same three sites. Mol. Endocrinol. 1997, 11, 1094-1102.
23. Syme, C. A.; Zhang, L.; Bisello, A., Caveolin-1 regulates cellular trafficking and function of the glucagon-like peptide 1 receptor. Mol. Endocrinol. 2006, 20, 3400-3411.
24. Holst, J. J.; Deacon, C. F.; Vilsboll, T.; Krarup, T.; Madsbad, S., Glucagon-like peptide-1, glucose homeostasis and diabetes. Trends Mol. Med. 2008, 14, 161-168.
25. Thornton, K.; Gorenstein, D. G., Structure of glucagon-like peptide(7-36) amide in a dodecylphosphocholine micelle as determined by 2D NMR. Biochemistry 1994, 33, 3532-3539.
26. Neidigh, J. W.; Fesinmeyer, R. M.; Prickett, K. S.; Andersen, N. H., Exendin-4 and glucagon-like-peptide-1: NMR structural comparisons in the solution and micelle-associated states. Biochemistry 2001, 40, 13188-13200.
27. Ahn, J.-M.; Gitu, P. M.; Medeiros, M.; Swift, J.; Trivedi, D.; Hruby, V. J., A new approach to search for the bioactive conformation of glucagon: positional cyclization scanning J. Med. Chem. 2001, 44, 3109-3116.
28. Murage, E. N.; Schroeder, J. C.; Beinborn, M.; Ahn, J.-M., Search for α-helical propensity in the receptor-bound conformation of glucagon-like peptide-1. Bioorg. Med. Chem. 2008, 16, 10106-10112.
29. Guibé, F.; Dangles, O.; Balavoine, G., Use of an allylic anchor group and of its palladium catalyzed hydrostannolytic cleavage in the solid-phase synthesis of protected peptide fragments. Tetrahedron Lett. 1989, 30, 2641-2644.
30. Tibaduiza, E. C.; Chen, C.; Beinborn, M., A small molecule ligand of the glucagon-like peptide 1 receptor targets its amino-terminal hormone binding domain. J. Biol. Chem. 2001, 276, 37787-37793.
31. Arulmozhi, D. K.; Portha, B., GLP-1 based therapy for type 2 diabetes. Eur. J. Pharmacol. Sci. 2006, 28, 96-108.
32. Hupe-Sodmann, K.; McGregor, G. P.; Bridenbaugh, R.; Goke, R.; Goke, B.; Thole, H.; Zimmermann, B.; Voigt, K., Characterisation of the processing by human neutral endopeptidase 24.11 of GLP-1(7-36)amide and comparison of the substrate specificity of the enzyme for other glucagon-like peptides. Regul. Pept. 1995, 58, 149-156.
33. Mammen, M.; Choi, S.-K.; Whitesides, G. M., Polyvalent interactions in biological systems: Implications for design and use of multivalent ligands and inhibitors. Angew. Chem. Int. Ed. 1998, 37, 2754-2794.
34. Terskikh, A. V.; Le Doussal, J. M.; Crameri, R.; Fisch, I.; Mach, J. P.; Kajava, A. V., "Peptabody": a new type of high avidity binding protein. Proc. Natl. Acad. Sci. U.S.A. 1997, 94, 1663-1668.
35. Fréchet, J. M. J., Dendrimers and supramolecular chemistry. Proc. Natl. Acad. Sci. U.S.A. 2002, 99, 4782-4787.
36. Dijkgraaf, I.; Rijnders, A. Y.; Soede, A.; Dechesne, A. C.; van Esse, G. W.; Brouwer, A. J.; Corstens, F. H. M.; Boerman, O. C.; Rijkers, D. T. S.; Liskamp, R. M. J., Synthesis of DOTA-conjugated multivalent cyclic-RGD peptide dendrimers via 1,3-dipolar cycloaddition and their biological evaluation: Implications for tumor targeting and tumor imaging purposes. Org. Biomol. Chem. 2007, 5, 935-944.
37. Sun, X.; Anderson, C. J., Production and applications of copper-64 radiopharmaceuticals. Methods Enzymol. 2004, 386, 237-261.
38. Boswell, C. A.; Sun, X.; Niu, W.; Weisman, G. R.; Wong, E. H.; Rheingold, A. L.; Anderson, C. J., Comparative in vivo stability of copper-64-labeled cross-bridged and conventional tetraazamacrocyclic complexes. J. Med. Chem. 2004, 47, 1465-1474.
39. Sun, X.; Wuest, M.; Weisman, G. R.; Wong, E. H.; Reed, D. P.; Boswell, C. A.; Motekaitis, R.; Martell, A. E.; Welch, M. J.; Anderson, C. J., Radiolabeling and in vivo behavior of copper-64-labeled cross-bridged cyclam ligands. J. Med. Chem. 2002, 45, 469-477.
40. Giraldi, A.; Persson, K.; Werkstrom, V.; Alm, P.; Wagner, G.; Andersson, K. E., Effects of diabetes on neurotransmission in rat vaginal smooth muscle. Int. J. Impot. Res. 2001, 13, 58-66.
41. Kim, N. N.; Stankovic, M.; Cushman, T. T.; Goldstein, I.; Munarriz, R.; Traish, A. M., Streptozotocin-induced diabetes in the rat is associated with changes in vaginal hemodynamics, morphology and biochemical markers. BMC Physiol. 2006, 6, 4.
42. Usta, M. F.; Bivalacqua, T. J.; Yang, D. Y.; Ramanitharan, A.; Sell, D. R.; Viswanathan, A.; Monnier, V. M.; Hellstrom, W. J., The protective effect of aminoguanidine on erectile function in streptozotocin diabetic rats. J. Urol. 2003, 170, 1437-1442.
43. Garofano, A.; Czernichow, P.; Breant, B., Impaired beta-cell regeneration in perinatally malnourished rats: a study with STZ. FASEB J. 2000, 14, 2611-2617.
44. Butler, A. E.; Janson, J.; Bonner-Weir, S.; Ritzel, R.; Rizza, R. A.; Butler, P. C., Beta-cell deficit and increased beta-cell apoptosis in humans with type 2 diabetes. Diabetes 2003, 52, 102-110.
45. Paris, M.; Bernard-Kargar, C.; Berthault, M. F.; Bouwens, L.; Ktorza, A., Specific and combined effects of insulin and glucose on functional pancreatic beta-cell mass in vivo in adult rats. Endocrinology 2003, 144, 2717-2727.
46. Souza, F.; Simpson, N.; Raffo, A.; Saxena, C.; Maffei, A.; Hardy, M.; Kilbourn, M.; Goland, R.; Leibel, R.; Mann, J. J.; Van Heertum, R.; Harris, P. E., Longitudinal noninvasive PET-based beta cell mass estimates in a spontaneous diabetes rat model. J. Clin. Invest. 2006, 116, 1506-1513.
47. Simpson, N. R.; Souza, F.; Witkowski, P.; Maffei, A.; Raffo, A.; Herron, A.; Kilbourn, M.; Jurewicz, A.; Herold, K.; Liu, E.; Hardy, M. A.; Van Heertum, R.; Harris, P. E., Visualizing pancreatic beta-cell mass with [11C]DTBZ. 2006, 33, 855-864.

48. Souza, F.; Freeby, M.; Hultman, K.; Simpson, N.; Herron, A.; Witkowski, P.; Liu, E.; Maffei, A.; Harris, P. E., Current progress in non-invasive imaging of beta cell mass of the endocrine pancreas. Curr. Med. Chem. 2006, 13, 2761-2773.

49. de Jong, M.; Rolleman, E. J.; Bernard, B. F.; Visser, T. J.; Bakker, W. H.; Breeman, W. A.; Krenning, E. P. Inhibition of renal uptake of indium-111-DTPA-octreotide in vivo. 1996, J. Nucl. Med. 37, 1388-1392.

50. Jamar, F.; Barone, R.; Mathieu, I.; Walrand, S.; Labar, D.; Carlier, P.; de Camps, J.; Schran, H.; Chen, T.; Smith, M. C.; Bouterfa, H.; Valkema, R.; Krenning, E. P.; Kvols, L. K.; Pauwels, S. 86Y-DOTA0)-D-Phe1-Tyr3-octreotide (SMT487)-A phase 1 clinical study: pharmacokinetics, biodistribution and renal protective effect of different regimens of amino acid co-infusion. 2003, Eur. J. Nucl. Med. Mol. Imaging 30, 510-518.

51. Rolleman, E. J.; Valkema, R.; de Jong, M.; Kooij, P. P.; Krenning, E. P. Safe and effective inhibition of renal uptake of radiolabelled octreotide by a combination of lysine and arginine. 2003, Eur. J. Nucl. Med. Mol. Imaging 30, 9-15.

What is claimed is:

1. An imaging agent comprising:
a bicyclic peptide analogue corresponding to a portion of a GLP-1 peptide that binds specifically to a GLP-1 receptor (GLP-1R), wherein the bicyclic analogue has two lactam bridges, and salts thereof, and wherein the bicyclic analogue is more stable than a non-cyclic analogue when incubated in the presence of enzymes that degrade GLP-1 and has an increased serum half-life;
a linker molecule connected to the portion of a peptide or protein; and
an imaging molecule connected to the linker molecule.

2. A imaging composition comprising:
a bicyclic peptide analogue with over 75% sequence homology to residues 7-36 of GLP-1 and having two lactam bridges, located between the positions 7 and 36 of GLP-1, or a salt thereof, wherein the agent is more stable than a non-cyclic analogue when incubated in the presence of enzymes that degrade GLP-1 and have an increased serum half-life and wherein at least a portion of the analogue binds specifically to a GLP-1 receptor (GLP-1R);
a linker molecule connected to the at least a portion of an analogue; and
an imaging molecule connected to the linker molecule.

3. The composition of claim 2, wherein the at least a portion of an analogue is selected from at least one of: SEQ ID No: 5, 6, 7, 8, 9, 10, 11, 12, 13, 14, 15, 16, 17, 18, 19, and salts thereof.

4. The composition of claim 2, wherein the linker molecule is monovalent or multivalent.

5. The composition of claim 2, wherein the imaging molecule comprises at least one of a radiolabel, an enzyme, a fluorescent label, a luminescent label, a bioluminescent label, a magnetic label, and biotin.

6. The composition of claim 2, wherein the imaging molecule comprises at least one of $^{18}F$, $^{68}Ga$, $^{60/61/62/64}Cu$, $^{89}Zr$, $^{86}Y$, $^{124}I$, $^{99m}Tc$, $^{94m}Tc$, $^{111}In$, $^{67}Ga$, $^{125}I$, $^{123}I$, $^{177}Lu$, $^{75/76/77}Br$, $^{166}Ho$, and $^{153}Sm$.

7. The composition of claim 2, wherein the composition is comprised in a pharmaceutically acceptable excipient.

8. The composition of claim 2, wherein the bicycle peptide analogue has an increased resistance to proteolytic cleavage by dipeptidyl peptidase-IV (DPP-IV), neutral endopeptidase (NEP 24.11), or both.

9. The composition of claim 2, wherein the composition comprises one or more positron emission tomography (PET) labels, single photon emission computed tomography (SPECT) labels, radioscintigraphy labels, or magnetic resonance imaging (MRI) labels.

10. A method of imaging a pancreas comprising:
injecting into a patient in need of pancreatic imaging an effective amount of an imaging agent comprising:
at least a portion of a bicyclic peptide analogue with over 75% sequence homology to residues 7-36 of GLP-1 with two lactam bridges, and salts thereof, between the positions 7 and 36 of GLP-1, salts thereof, wherein the agent is more stable than a non-cyclic analogue when incubated in the presence of enzymes that degrade GLP-1 and has an increased serum half-live,
a linker molecule connected to the at least a portion of a peptide analogue, and
an imaging molecule connected to the linker molecule; and
recording an image of the patient in need of pancreatic imaging.

11. The method of claim 10, wherein the at least a portion of an analogue is selected from at least one of: SEQ ID No: 5, 6, 7, 8, 9, 10, 11, 12, 13, 14, 15, 16, 17, 18, 19, and salts or derivatives thereof.

12. The method of claim 10, wherein the linker molecule is monovalent or multivalent.

13. The method of claim 10, wherein the imaging molecule comprises at least one of a radiolabel, an enzyme, a fluorescent label, a luminescent label, a bioluminescent label, a magnetic label, and biotin.

14. The method of claim 10, wherein the imaging molecule further comprises at least one of $^{18}F$, $^{68}Ga$, $^{60/61/62/64}Cu$, $^{89}Zr$, $^{86}Y$, $^{124}I$, $^{99m}Tc$, $^{94m}Tc$, $^{111}In$, $^{67}Ga$, $^{125}I$, $^{123}I$, $^{177}Lu$, $^{75/76/77}Br$, $^{166}Ho$, and $^{153}Sm$.

15. The method of claim 10, wherein the imaging agent further comprises a pharmaceutically acceptable excipient.

16. The method of claim 10, wherein the imaging agent has an increased resistance to proteolytic cleavage by dipeptidyl peptidase-IV (DPP-IV), neutral endopeptidase (NEP 24.11), or both.

17. The method of claim 10, wherein the imaging agent is an organ specific imaging agent comprises one or more labels that made the agent detectable by positron emission tomography (PET), single photon emission computed tomography (SPECT), radioscintigraphy, or magnetic resonance imaging (MRI).

18. An imaging agent comprising:
at least one analogue selected from SEQ ID No: 5, 6, 7, 8, 9, 10, 11, 12, 13, 14, 15, 16, 17, 18, 19, salts or derivatives thereof, wherein the peptide is bicyclic and comprises two lactam bridges, and wherein agent is more stable than a non-cyclic analogue when incubated in the presence of enzymes that degrade GLP-1 and has an increased serum half-life;
a linker molecule connected to the at least a portion of an analogue; and
an imaging molecules connected to the linker molecule.

19. The imaging agent of claim 18, wherein the linker molecule is multivalent and conjugated to at least one additional bicyclic GLP-1 analogue.

20. The imaging agent of claim 18, wherein the agent further comprises at least one of a radiolabel, an enzyme, a fluorescent label, a luminescent label, a bioluminescent label, a magnetic label, and biotin.

21. The imaging agent of claim 18, wherein the imaging molecule further comprises at least one of $^{18}$F, $^{68}$Ga, $^{60/61/62/64}$Cu, $^{89}$Zr, $^{86}$Y, $^{124}$I, $^{99m}$Tc, $^{94m}$Tc, $^{111}$In, $^{67}$Ga, $^{125}$I, $^{123}$I, $^{177}$Lu, $^{75/76/77}$Br, $^{166}$Ho, and $^{153}$Sm.

22. The imaging agent of claim 18, wherein the imaging agent is comprised in a pharmaceutically acceptable excipient.

23. The imaging agent of claim 18, wherein the imaging agent has an increased resistance to proteolytic cleavage by dipeptidyl peptidase-IV (DPP-IV), neutral endopeptidase (NEP 24.11), or both.

24. The imaging agent of claim 18, wherein the imaging agent is an organ specific imaging agent comprising one or more positron emission tomography (PET) labels, single photon emission computed tomography (SPECT) labels, radioscintigraphy labels, or magnetic resonance imaging (MRI) labels.

25. An imaging agent comprising:
(i) the bicyclic peptide analogue SEQ ID NO: 12 comprising two lactam bridges, one at positions 18 and 22 and one at positions 30 and 34;
(ii) a linker molecule connected to the peptide; and
(iii) an imaging molecule connected to the linker molecule.

* * * * *

UNITED STATES PATENT AND TRADEMARK OFFICE
CERTIFICATE OF CORRECTION

PATENT NO. : 8,992,886 B2  
APPLICATION NO. : 13/263320  
DATED : March 31, 2015  
INVENTOR(S) : Jung-Mo Ahn and Xiankai Sun Page 1 of 1

It is certified that error appears in the above-identified patent and that said Letters Patent is hereby corrected as shown below:

In the Claims,

In claim 8, column 40, line 27, delete "bicycle" and insert --bicyclic-- therefor.

In claim 17, column 41, line 8, delete "comprises" and insert --comprising-- therefor.

In claim 18, column 41, line 23, delete "molecules" and insert --molecule-- therefor.

Signed and Sealed this  
Twenty-first Day of July, 2015

Michelle K. Lee  
*Director of the United States Patent and Trademark Office*

SEQUENCE LISTING

```
<160> NUMBER OF SEQ ID NOS: 34

<210> SEQ ID NO 1
<211> LENGTH: 30
<212> TYPE: PRT
<213> ORGANISM: artificial sequence
<220> FEATURE:
<223> OTHER INFORMATION: synthetic peptide

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 39
<212> TYPE: PRT
<213> ORGANISM: Artificial sequence
<220> FEATURE:
<223> OTHER INFORMATION: synthetic peptide

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 31
<212> TYPE: PRT
<213> ORGANISM: artificial sequence
<220> FEATURE:
<223> OTHER INFORMATION: synthetic peptide

<400> SEQUENCE: 3

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 4
<211> LENGTH: 39
<212> TYPE: PRT
<213> ORGANISM: artificial sequence
<220> FEATURE:
<223> OTHER INFORMATION: synthetic peptide

<400> SEQUENCE: 4

His Ser Asp Gly Thr Phe Thr Ser Asp Leu Ser Lys Gln Met Glu Glu
1               5                   10                  15
```

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 5
<211> LENGTH: 30
<212> TYPE: PRT
<213> ORGANISM: artificial sequence
<220> FEATURE:
<223> OTHER INFORMATION: synthetic peptide

<400> SEQUENCE: 5

His Ala Glu Gly Thr Phe Thr Ser Asp Glu Ser Ser Tyr Lys Glu Gly
1               5                   10                  15

Gln Ala Ala Lys Glu Phe Ile Ala Trp Leu Val Lys Gly Arg
            20                  25                  30

<210> SEQ ID NO 6
<211> LENGTH: 30
<212> TYPE: PRT
<213> ORGANISM: artificial sequence
<220> FEATURE:
<223> OTHER INFORMATION: synthetic peptide

<400> SEQUENCE: 6

His Ala Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg
            20                  25                  30

<210> SEQ ID NO 7
<211> LENGTH: 30
<212> TYPE: PRT
<213> ORGANISM: artificial sequence
<220> FEATURE:
<223> OTHER INFORMATION: synthetic peptide

<400> SEQUENCE: 7

His Ala Glu Gly Thr Phe Thr Ser Asp Glu Ser Ser Tyr Lys Glu Gly
1               5                   10                  15

Gln Ala Ala Lys Glu Phe Ile Glu Trp Leu Val Lys Gly Arg
            20                  25                  30

<210> SEQ ID NO 8
<211> LENGTH: 30
<212> TYPE: PRT
<213> ORGANISM: artificial sequence
<220> FEATURE:
<223> OTHER INFORMATION: synthetic peptide

<400> SEQUENCE: 8

His Ala Glu Gly Thr Phe Thr Ser Asp Val Ser Glu Tyr Leu Glu Lys
1               5                   10                  15

Gln Ala Ala Lys Glu Phe Ile Glu Trp Leu Val Lys Gly Arg
            20                  25                  30

<210> SEQ ID NO 9
<211> LENGTH: 30
<212> TYPE: PRT
<213> ORGANISM: artificial sequence
<220> FEATURE:
<223> OTHER INFORMATION: synthetic peptide
<220> FEATURE:

```
<221> NAME/KEY: misc_feature
<222> LOCATION: (2)..(2)
<223> OTHER INFORMATION: X is D-Ala

<400> SEQUENCE: 9

His Xaa Glu Gly Thr Phe Thr Ser Asp Glu Ser Ser Tyr Lys Glu Gly
1               5                   10                  15

Gln Ala Ala Lys Glu Phe Ile Ala Trp Leu Val Lys Gly Arg
            20                  25                  30

<210> SEQ ID NO 10
<211> LENGTH: 30
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: X is D-Ala

<400> SEQUENCE: 10

His Xaa Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg
            20                  25                  30

<210> SEQ ID NO 11
<211> LENGTH: 30
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: X is D-Ala

<400> SEQUENCE: 11

His Xaa Glu Gly Thr Phe Thr Ser Asp Glu Ser Ser Tyr Lys Glu Gly
1               5                   10                  15

Gln Ala Ala Lys Glu Phe Ile Glu Trp Leu Val Lys Gly Arg
            20                  25                  30

<210> SEQ ID NO 12
<211> LENGTH: 30
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: X is D-Ala

<400> SEQUENCE: 12

His Xaa Glu Gly Thr Phe Thr Ser Asp Val Ser Glu Tyr Leu Glu Lys
1               5                   10                  15

Gln Ala Ala Lys Glu Phe Ile Glu Trp Leu Val Lys Gly Arg
            20                  25                  30

<210> SEQ ID NO 13
<211> LENGTH: 30
<212> TYPE: PRT
<213> ORGANISM: artificial sequence
<220> FEATURE:
<223> OTHER INFORMATION: synthetic peptide
```

```
<400> SEQUENCE: 13

His Ala Glu Gly Thr Phe Thr Ser Asp Val Ser Glu Tyr Leu Glu Lys
1               5                   10                  15

Gln Ala Ala Lys Glu Phe Ile Ala Trp Leu Val Lys Gly Arg
            20                  25                  30

<210> SEQ ID NO 14
<211> LENGTH: 30
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: X is D-Ala

<400> SEQUENCE: 14

His Xaa Glu Gly Thr Phe Thr Ser Asp Val Ser Glu Tyr Leu Glu Lys
1               5                   10                  15

Gln Ala Ala Lys Glu Phe Ile Ala Trp Leu Val Lys Gly Arg
            20                  25                  30

<210> SEQ ID NO 15
<211> LENGTH: 30
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: X is AiB, 2-Aminoisobutyric acid

<400> SEQUENCE: 15

His Xaa Glu Gly Thr Phe Thr Ser Asp Glu Ser Ser Tyr Lys Glu Gly
1               5                   10                  15

Gln Ala Ala Lys Glu Phe Ile Ala Trp Leu Val Lys Gly Arg
            20                  25                  30

<210> SEQ ID NO 16
<211> LENGTH: 30
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: X is AiB, 2-Aminoisobutyric acid

<400> SEQUENCE: 16

His Xaa Glu Gly Thr Phe Thr Ser Asp Val Ser Glu Tyr Leu Glu Lys
1               5                   10                  15

Gln Ala Ala Lys Glu Phe Ile Ala Trp Leu Val Lys Gly Arg
            20                  25                  30

<210> SEQ ID NO 17
<211> LENGTH: 30
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (2)..(2)
```

<223> OTHER INFORMATION: X is AiB, 2-Aminoisobutyric acid

<400> SEQUENCE: 17

His Xaa Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg
            20                  25                  30

<210> SEQ ID NO 18
<211> LENGTH: 30
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: X is AiB, 2-Aminoisobutyric acid

<400> SEQUENCE: 18

His Xaa Glu Gly Thr Phe Thr Ser Asp Glu Ser Ser Tyr Lys Glu Gly
1               5                   10                  15

Gln Ala Ala Lys Glu Phe Ile Glu Trp Leu Val Lys Gly Arg
            20                  25                  30

<210> SEQ ID NO 19
<211> LENGTH: 30
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: X is AiB, 2-Aminoisobutyric acid

<400> SEQUENCE: 19

His Xaa Glu Gly Thr Phe Thr Ser Asp Val Ser Glu Tyr Leu Glu Lys
1               5                   10                  15

Gln Ala Ala Lys Glu Phe Ile Glu Trp Leu Val Lys Gly Arg
            20                  25                  30

<210> SEQ ID NO 20
<211> LENGTH: 39
<212> TYPE: PRT
<213> ORGANISM: artificial sequence
<220> FEATURE:
<223> OTHER INFORMATION: synthetic peptide

<400> SEQUENCE: 20

His Gly Glu Gly Thr Phe Thr Ser Asp Glu Ser Lys Gln Lys Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 21
<211> LENGTH: 39
<212> TYPE: PRT
<213> ORGANISM: artificial sequence
<220> FEATURE:
<223> OTHER INFORMATION: synthetic peptide

<400> SEQUENCE: 21

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Lys Gly Gly Pro Ser
            20                  25                  30

Ser Gly Ala Pro Pro Pro Ser
        35

<210> SEQ ID NO 22
<211> LENGTH: 39
<212> TYPE: PRT
<213> ORGANISM: artificial sequence
<220> FEATURE:
<223> OTHER INFORMATION: synthetic peptide

<400> SEQUENCE: 22

His Gly Glu Gly Thr Phe Thr Ser Asp Leu Ser Glu Gln Met Glu Lys
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 23
<211> LENGTH: 39
<212> TYPE: PRT
<213> ORGANISM: artificial sequence
<220> FEATURE:
<223> OTHER INFORMATION: synthetic peptide

<400> SEQUENCE: 23

His Gly Glu Gly Thr Phe Thr Ser Asp Glu Ser Lys Gln Lys Glu Glu
1               5                   10                  15

Glu Ala Val Arg Leu Phe Ile Glu Trp Leu Lys Lys Gly Gly Pro Ser
            20                  25                  30

Ser Gly Ala Pro Pro Pro Ser
        35

<210> SEQ ID NO 24
<211> LENGTH: 39
<212> TYPE: PRT
<213> ORGANISM: artificial sequence
<220> FEATURE:
<223> OTHER INFORMATION: synthetic peptide

<400> SEQUENCE: 24

His Gly Glu Gly Thr Phe Thr Ser Asp Leu Ser Glu Gln Met Glu Lys
1               5                   10                  15

Glu Ala Val Arg Leu Phe Ile Glu Trp Leu Lys Lys Gly Gly Pro Ser
            20                  25                  30

Ser Gly Ala Pro Pro Pro Ser
        35

<210> SEQ ID NO 25
<211> LENGTH: 39
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (8)..(8)
<223> OTHER INFORMATION: X is AiB, 2-Aminoisobutyric acid

<400> SEQUENCE: 25

His Gly Glu Gly Thr Phe Thr Xaa Asp Glu Ser Lys Gln Lys Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 26
<211> LENGTH: 39
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (8)..(8)
<223> OTHER INFORMATION: X is AiB, 2-Aminoisobutyric acid

<400> SEQUENCE: 26

His Gly Glu Gly Thr Phe Thr Xaa Asp Leu Ser Glu Gln Met Glu Lys
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 27
<211> LENGTH: 39
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (8)..(8)
<223> OTHER INFORMATION: X is AiB, 2-Aminoisobutyric acid

<400> SEQUENCE: 27

His Gly Glu Gly Thr Phe Thr Xaa Asp Leu Ser Lys Gln Met Glu Glu
1               5                   10                  15

Glu Ala Val Arg Leu Phe Ile Glu Trp Leu Lys Lys Gly Gly Pro Ser
            20                  25                  30

Ser Gly Ala Pro Pro Pro Ser
        35

<210> SEQ ID NO 28
<211> LENGTH: 39
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (8)..(8)
<223> OTHER INFORMATION: X is AiB, 2-Aminoisobutyric acid

<400> SEQUENCE: 28

His Gly Glu Gly Thr Phe Thr Xaa Asp Glu Ser Lys Gln Lys Glu Glu
1               5                   10                  15

Glu Ala Val Arg Leu Phe Ile Glu Trp Leu Lys Lys Gly Gly Pro Ser
            20                  25                  30

Ser Gly Ala Pro Pro Pro Ser
        35

```
<210> SEQ ID NO 29
<211> LENGTH: 39
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (8)..(8)
<223> OTHER INFORMATION: X is AiB, 2-Aminoisobutyric acid

<400> SEQUENCE: 29

His Gly Glu Gly Thr Phe Thr Xaa Asp Leu Ser Glu Gln Lys Glu
1               5                   10                  15

Glu Ala Val Arg Leu Phe Ile Glu Trp Leu Lys Lys Gly Gly Pro Ser
            20                  25                  30

Ser Gly Ala Pro Pro Pro Ser
        35

<210> SEQ ID NO 30
<211> LENGTH: 30
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: X is D-Ala

<400> SEQUENCE: 30

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 31
<211> LENGTH: 30
<212> TYPE: PRT
<213> ORGANISM: artificial sequence
<220> FEATURE:
<223> OTHER INFORMATION: synthetic peptide

<400> SEQUENCE: 31

His Ala Glu Gly Thr Phe Thr Ser Asp Val Ser Ser Tyr Leu Glu Lys
1               5                   10                  15

Gln Ala Ala Glu Glu Phe Ile Ala Trp Leu Val Lys Gly Arg
            20                  25                  30

<210> SEQ ID NO 32
<211> LENGTH: 30
<212> TYPE: PRT
<213> ORGANISM: artificial sequence
<220> FEATURE:
<223> OTHER INFORMATION: synthetic peptide

<400> SEQUENCE: 32

His Ala Glu Gly Thr Phe Thr Ser Asp Val Ser Ser Tyr Leu Glu Gly
1               5                   10                  15

Lys Ala Ala Lys Glu Phe Ile Ala Trp Leu Val Lys Gly Arg
            20                  25                  30

<210> SEQ ID NO 33
<211> LENGTH: 30
<212> TYPE: PRT
```

```
<213> ORGANISM: artificial sequence
<220> FEATURE:
<223> OTHER INFORMATION: synthetic peptide

<400> SEQUENCE: 33

His Ala Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg
            20                  25                  30

<210> SEQ ID NO 34
<211> LENGTH: 30
<212> TYPE: PRT
<213> ORGANISM: artificial sequence
<220> FEATURE:
<223> OTHER INFORMATION: synthetic peptide

<400> SEQUENCE: 34

His Ala Glu Gly Thr Phe Thr Ser Asp Val Ser Ser Tyr Leu Glu Gly
1               5                   10                  15

Gln Ala Ala Lys Glu Phe Ile Lys Trp Leu Val Glu Gly Arg
            20                  25                  30
```